United States Patent
Dahl et al.

(10) Patent No.: US 10,619,132 B2
(45) Date of Patent: Apr. 14, 2020

(54) TISSUE-ENGINEERED CONSTRUCTS

(71) Applicant: Humacyte, Inc., Morrisville, NC (US)

(72) Inventors: Shannon L. M. Dahl, Durham, NC (US); Laura E. Niklason, Greenwich, CT (US); Justin T. Strader, Cary, NC (US); William E. Tente, Seekonk, MA (US); Joseph J. Lundquist, Durham, NC (US)

(73) Assignee: Humacyte, Inc., Durham, NC (US)

( * ) Notice: Subject to any disclaimer, the term of this patent is extended or adjusted under 35 U.S.C. 154(b) by 0 days.

(21) Appl. No.: 15/595,560

(22) Filed: May 15, 2017

(65) Prior Publication Data
US 2017/0306292 A1 Oct. 26, 2017

Related U.S. Application Data

(63) Continuation of application No. 14/495,310, filed on Sep. 24, 2014, now Pat. No. 9,650,603, and a
(Continued)

(51) Int. Cl.
*C12N 5/00* (2006.01)
*A61F 2/06* (2013.01)
(Continued)

(52) U.S. Cl.
CPC .............. *C12N 5/0068* (2013.01); *A61F 2/04* (2013.01); *A61F 2/06* (2013.01); *A61L 27/16* (2013.01); *A61L 27/18* (2013.01); *A61L 27/34* (2013.01); *A61L 27/3633* (2013.01); *A61L 27/38* (2013.01); *A61L 27/3895* (2013.01); *A61L 27/54* (2013.01); *A61L 27/58* (2013.01); *B29C 53/005* (2013.01); *B29C 53/36* (2013.01); *A61F 2002/047* (2013.01); *A61F 2002/048* (2013.01);
(Continued)

(58) Field of Classification Search
CPC ........................................................ C12N 5/00
USPC .. 623/1.46–1.54, 23.64–23.68, 23.72–23.76; 435/395–403; 156/218; 424/422–426
See application file for complete search history.

(56) References Cited

U.S. PATENT DOCUMENTS 5,197,977 A 3/1993 Hoffman et al.
5,830,708 A 11/1998 Naughton
(Continued)

FOREIGN PATENT DOCUMENTS

EP 1698358 A1 9/2006
WO WO2002040630 5/2002
WO WO2012094611 7/2012

OTHER PUBLICATIONS

Basu et al., "Platform technologies for tubular organ regeneration," *Trends Biotechnol*, 28(10):526-533, (2010).
(Continued)

*Primary Examiner* — Yashita Sharma
(74) *Attorney, Agent, or Firm* — Cooley LLP

(57) ABSTRACT

The present invention provides constructs including a tubular biodegradable polyglycolic acid scaffold, wherein the scaffold may be coated with extracellular matrix proteins and substantially acellular. The constructs can be utilized as an arteriovenous graft, a coronary graft, a peripheral artery bypass conduit, or a urinary conduit. The present invention also provides methods of producing such constructs.

14 Claims, 15 Drawing Sheets

Related U.S. Application Data continuation of application No. 14/495,339, filed on Sep. 24, 2014, now Pat. No. 9,657,265, said application No. 14/495,310 is a continuation of application No. 13/978,422, filed as application No. PCT/US2012/020513 on Jan. 6, 2012, now Pat. No. 9,556,414.

(60) Provisional application No. 61/430,381, filed on Jan. 6, 2011.

(51) Int. Cl.

| | | |
|---|---|---|
| A61L 27/34 | (2006.01) | |
| A61F 2/04 | (2013.01) | |
| B29C 53/00 | (2006.01) | |
| B29C 53/36 | (2006.01) | |
| A61L 27/16 | (2006.01) | |
| A61L 27/18 | (2006.01) | |
| A61L 27/36 | (2006.01) | |
| A61L 27/38 | (2006.01) | |
| A61L 27/54 | (2006.01) | |
| A61L 27/58 | (2006.01) | |
| B29K 67/00 | (2006.01) | |
| B29K 105/00 | (2006.01) | |
| B29L 23/00 | (2006.01) | |
| B29L 31/00 | (2006.01) | |

(52) U.S. Cl.
CPC .. *B29K 2067/043* (2013.01); *B29K 2105/256* (2013.01); *B29K 2995/006* (2013.01); *B29K 2995/0056* (2013.01); *B29L 2023/00* (2013.01); *B29L 2031/7532* (2013.01); *C12N 2533/30* (2013.01); *C12N 2533/40* (2013.01); *Y10T 156/1038* (2015.01)

(56) References Cited

U.S. PATENT DOCUMENTS

| | | | |
|---|---|---|---|
| RE36,370 E | 11/1999 | Li | |
| 6,231,615 B1 | 5/2001 | Preissman | |
| 6,428,802 B1 | 8/2002 | Atala | |
| 6,786,919 B1* | 9/2004 | Escano | A61F 2/90 606/194 |
| 7,918,897 B2 | 4/2011 | Bertram et al. | |
| 7,943,378 B2 | 5/2011 | Niklason et al. | |
| 8,337,485 B2 | 12/2012 | Ludlow et al. | |
| 2001/0016772 A1* | 8/2001 | Lee | A61L 27/3804 623/14.12 |
| 2002/0035394 A1 | 3/2002 | Fierens et al. | |
| 2002/0090725 A1 | 7/2002 | Simpson et al. | |
| 2002/0106793 A1 | 8/2002 | West et al. | |
| 2002/0115208 A1 | 8/2002 | Mitchell et al. | |
| 2003/0072741 A1 | 4/2003 | Berglund et al. | |
| 2003/0235562 A1 | 12/2003 | Niklason et al. | |
| 2006/0240061 A1 | 10/2006 | Atala et al. | |
| 2007/0248933 A1 | 10/2007 | Rutherford et al. | |
| 2008/0268016 A1* | 10/2008 | Fang | A61K 35/22 424/423 |
| 2009/0012607 A1 | 1/2009 | Kim et al. | |
| 2009/0018643 A1* | 1/2009 | Hashi | A61F 2/82 623/1.15 |
| 2009/0130221 A1 | 5/2009 | Bolland et al. | |
| 2009/0163990 A1 | 6/2009 | Yang et al. | |
| 2009/0202432 A1 | 8/2009 | Schenk et al. | |
| 2010/0145473 A1 | 6/2010 | Yannas et al. | |
| 2010/0310623 A1 | 12/2010 | Laurencin et al. | |

OTHER PUBLICATIONS

Dahl, et al., "Readily Available Tissue-Engineered Vascular Grafts," *Sci Transl Med* 2, 3, 68ra9 (2011).
Dahl, et al., "Decellularized native and engineered arterial scaffolds for transplantation," *Cell Transplant*, 12(6):659-666 (2003).
Dahl, et al., "Mechanical properties and compositions of tissue engineered and native arteries," *Ann Biomed Eng*, 35(3):348-355 (2007).
Dai, et al., "Reconstruction of lymph vessel by lymphatic endothelial cells combined with polyglycolic acid scaffolds: a pilot study." J Biotechnol. Oct. 1, 2010;150(1):182-9. doi: 10.1016/j.jbiotec.2010. 07.028. Epub Aug. 4, 2010.
Gui, et al, "Novel Utilization of Serum in Tissue Decellularization" Apr. 2010, published online Jun. 30, 2009, Tissue Engineering: Part C, vol. 16, No. 2: 173-184.
Hopkins, et al., "Decellularization reduces calcification while improving both durability and 1-year functional results of pulmonary homograft valves in juvenile sheep" (2009), Journal of Thoracic and Cardiovascular Surgery, vol. 137, No. 4: 907-13.
McKee, et al., "Human arteries engineered in vitro," *EMBO Rep*, 4(6):633-638 (2003).
Niklason, et al., "Functional arteries grown in vitro". *Science*, 284(5413):489-493 (1999).
Poh, et al., "Blood vessels engineered from human cells," *Lancet*, 365(9477):2122-2124 (2005).
Prichard, et al., "An early study on the mechanisms that allow tissue-engineered vascular grafts to resist intimal hyperplasia," *J Cardiovasc Transl Res*, 4(5):674-682 (2011).
Shahin and Doran, "Improved Seeding of Chondrocytes into Polyglycolic Acid Scaffolds Using Semi-Static and Alginate Loading Materials." Biotechnol. Prog., 2011, vol. 27(1): 191-200.
Shin'Oka, et al., "Midterm clinical result of tissue-engineered vascular autografts seeded with autologous bone marrow cells," *J Thorac Cardiovasc Surg*, 129(6):1330-1338 (2005).
Prabhakar V. et al. "Engineering porcine arteries: Effects of scaffold modification" Journal of Biomedical Materials Research, (2002), vol. 67 A, Issue 1, p. 303-311.
Pellegata et al. "Arterial Decellularized Scaffolds Produced Using an Innovative Automatic System" Cells Tissue Organs, 2014, vol. 200, p. 363-373.

* cited by examiner

CONDUIT BEFORE URINE EXPOSURE

CONDUIT AFTER URINE EXPOSURE FOR 4 WEEKS AT 37°C

TISSUE-ENGINEERED CONSTRUCTS

CROSS-REFERENCE TO RELATED APPLICATIONS

This application is a continuation of U.S. application Ser. No. 14/495,310, filed Sep. 24, 2014 and issued as U.S. Pat. No. 9,650,603, and U.S. application Ser. No. 14/495,339, filed Sep. 24, 2014 and issued as U.S. Pat. No. 9,657,265, each of which is a continuation of U.S. application Ser. No. 13/978,422, filed Sep. 12, 2013 and issued as U.S. Pat. No. 9,556,414, which is a United States national phase application under 35 U.S.C 371 of International Application No. PCT/US2012/020513, filed Jan. 6, 2012, which claims the benefit of U.S. Provisional Application No. 61/430,381, filed Jan. 6, 2011. The contents of the aforementioned patent applications are incorporated herein by reference in their entireties.

BACKGROUND OF THE INVENTION

There is a considerable need for vascular grafts when the patient's own vasculature is either unavailable because of prior harvest or unsuitable secondary to disease. Instances when a vascular graft might be needed include peripheral arterial disease, coronary artery disease, and hemodialysis access for patients with end stage renal disease. To date, the most successful vascular conduit for coronary or peripheral vascular surgery is the patient's own blood vessel, obtained from elsewhere in the body, often the greater saphenous vein in the leg. For patients requiring hemodialysis, the ideal access is a fistula, or a connection between the patient's own artery and vein.

When autologous vessels are not available, synthetic polytetrafluoroethylene (PTFE) grafts are often utilized for large diameter (≥6 mm) applications, such as arteriovenous access for hemodialysis (U.S. Renal Data System, "USRDS 2009 Annual Data Report: Atlas of Chronic Kidney Disease and End-Stage Renal Disease in the United States" (National Institutes of Health, National Institute of Diabetes and Digestive and Kidney Diseases, 2009) or above the knee peripheral arterial bypass. However, arteriovenous PTFE grafts for hemodialysis have a poor median patency of only 10 months because of infection, thrombus, or intimal hyperplasia-induced occlusion at either the distal anastomosis or outflow vein (U.S. Renal Data System; Schild, et al., *J Vasc Access* 9, 231-235 (2008)). Other types of grafts, such as decellularized bovine internal jugular xenografts and human allograft vessels from cadavers, are prone to aneurysm, calcification, and thrombosis, and therefore have not gained widespread clinical acceptance (Sharp et al., *Eur J Vasc Endovasc Surg* 27, 42-44 (2004); Dohmen et al., *Tex Heart Inst J* 30, 146-148 (2003); Madden et al., *Ann Vasc Surg* 19, 686-691 (2005)). In situations where small diameter (i.e., 3-4 mm) vessels are required, such as below the knee and coronary artery bypass grafting, the patient's own vasculature (i.e., internal mammary artery, saphenous vein) is predominantly used because synthetic grafts and allografts have unacceptably low patency rates (e.g., patency is <25% at 3 years using synthetic and cryopreserved grafts in peripheral and coronary bypass surgeries, compared to >70% for autologous vascular conduits) (Chard, et al., *J Thorac Cardiovasc Surg* 94, 132-134 (1987); Albers, et al., *Eur J Vasc Endovasc Surg* 28, 462-472 (2004); Laub, et al., *Ann Thorac Surg* 54, 826-831 (1992); Collins, et al., *Circulation* 117, 2859-2864 (2008); Harris et al., *J Vasc Surg* 33, 528-532 (2001); Albers, et al., *J Vasc Surg* 43, 498-503 (2006)). Thus, a readily available, versatile vascular graft with good patency that resists dilatation, calcification, and intimal hyperplasia would fill a substantial and growing clinical need.

To date, tissue engineered vascular grafts formed by seeding autologous bone marrow cells onto a copolymer of L-lactide and ε-caprolactone (Shin'oka, et al., *J Thorac Cardiovasc Surg* 129, 1330-1338 (2005)), or culturing autologous fibroblasts and endothelial cells (ECs) without a scaffold (McAllister, et al., *Lancet* 373, 1440-1446 (2009)), have shown promising functional results in early clinical trials. Thus far, only the latter has proven physically strong enough for use in the arterial circulation. This patient-specific graft requires a 6-9 month culture period in which the autologous fibroblasts produce sheets of tissue. The sheets are fused together around a stainless steel mandrel (4.8 mm diameter), inner fused layers are dehydrated, and the graft lumen is seeded with autologous ECs (McAllister, et al., *Lancet* 373, 1440-1446 (2009)). Because of high production costs (≥$15,000 per graft (McAllister, et al., *Regen Med* 3, 925-937 (2008)) and long wait time (up to 9 months) for patients that require expeditious intervention, it is unlikely that this approach will become standard clinical practice.

Thus, there is a need in the art for effective, rapidly available, reliable and cost-effective tissue engineered constructs that can function long term, with minimal to no side effects, in vivo.

SUMMARY OF THE INVENTION

The present invention provides a construct including a tubular non-woven, biodegradable polyglycolic acid scaffold, wherein the density of the polyglycolic acid is about 45 mg/cc to about 75 mg/cc and said density is uniform across the entire tubular scaffold.

The length of the tubular biodegradable polyglycolic acid scaffold can be about 1 cm to about 100 cm. Preferably, the length of the tubular biodegradable polyglycolic acid scaffold can be about 10 cm to about 40 cm. The inner diameter of the tubular biodegradable polyglycolic acid scaffold can be greater than about 3 mm. Preferably, the inner diameter of the tubular biodegradable polyglycolic acid scaffold can be about 3 mm to about 20 mm.

The thickness of the polyglycolic acid can be about 0.8 to about 1.5 mm and said thickness is uniform across the tubular scaffold. Preferably, the polyglycolic acid can be about 0.8 to about 1.2 mm and said thickness is uniform across the tubular scaffold. The thickness of the fibers within the polyglycolic acid can be about 5 to about 20 µm. The porosity of the polyglycolic acid can be about 90% to about 98%.

The constructs of the present invention can further include non-biodegradable polyethylene terephthalate supports at each end of the tubular biodegradable polyglycolic acid scaffold. The non-biodegradable polyethylene terephthalate supports can be attached to the tubular biodegradable polyglycolic acid scaffold by any means known in the art. Preferably, the polyethylene terephthalate supports are attached via sutures. The porosity of the polyethylene terephthalate can be ≥200 cc/min/cm$^2$. The tubular biodegradable polyglycolic acid scaffold and the non-biodegradable polyethylene terephthalate supports can permit the attachment and growth of cells. In other embodiments, other non-biodegradable polymers can be used to support each end of the tubular scaffold.

The constructs of the present invention are substantially free of heavy metal contaminants. Preferably, the construct includes only trace amounts of heavy metal contaminants selected from the group consisting of: aluminum, barium, calcium, iodine, lanthanum, magnesium, nickel, potassium and zinc.

The constructs of the present invention can further include extracellular matrix proteins within, and around, the biodegradable polyglycolic acid scaffold. Preferably, the thickness of the extracellular matrix proteins is greater than about 200 micrometers at the thinnest portion of the matrix.

The present invention also provides methods of producing a tubular polyglycolic acid construct including (a) providing a biodegradable polyglycolic acid sheet, wherein the density of the polyglycolic acid is about 45 mg/cc to about 75 mg/cc and the thickness of the polyglycolic acid sheet is about 0.8 to about 1.2 mm, (b) wrapping the polyglycolic acid sheet around a mandrel such that opposite edges of the polyglycolic acid sheet meet at an interface; (c) pulling polyglycolic acid fibers from each opposing edge of the sheet across the interface, and (d) forming a seam by entangling said pulled polyglycolic acid fibers from one side of the interface with the polyglycolic acid fibers on the opposite side of the interface, wherein the density of the polyglycolic acid at the seam is about 45 mg/cc to about 75 mg/cc and the thickness of the polyglycolic acid at the seam is about 0.8 to about 1.5 mm, thereby producing a tubular biodegradable polyglycolic acid construct with a uniform polyglycolic acid density. The present invention also provides a tubular biodegradable polyglycolic acid construct formed by the methods described herein.

The construct can be selected from the group consisting of an arteriovenous graft, a coronary graft, peripheral artery bypass conduit, fallopian tube replacement, and a urinary conduit. The mandrel can comprise any material known in the art. Preferably, the mandrel comprises a gas permeable, silicone tube.

The entangling step may be performed by any method known in the art which permits the seam to remain intact in subsequent treatment steps. Preferably, entangling is performed with a felting needle.

The methods of the present invention can further include, treating the tubular construct to remove heavy metal contaminants. Preferably, the tubular construct is treated with one or more non-polar solvents followed by treatment with a primary alcohol, such as ethanol. Preferably, the seam remains intact following said treatment. This treatment may also be performed on the biodegradable scaffold prior to formation of a tube.

The methods of the present invention can further include, treating the tubular construct to increase the rate of polyglycolic acid degradation and/or increase the wettability of the polyglycolic acid. Preferably, the tubular construct is treated with a strong base. More preferably, the strong base is 1M NaOH. Preferably, the seam remains intact following said treatment. This treatment may also be performed on the biodegradable scaffold prior to formation of a tube.

The methods of the present invention can further include, attaching non-biodegradable polyethylene terephthalate supports at end of the tubular biodegradable polyglycolic acid scaffold.

The present invention also provides a tubular construct comprising extracellular matrix proteins and polyglycolic acid having an internal diameter of ≥3 mm, wherein the construct is immune and calcification resistant, wherein the polyglycolic acid comprises less than 33% of the cross-sectional area of said construct and wherein the construct is substantially acellular comprising less than 5% cells, less than 2% cells, less than 1% cells or contains no cells. Preferably, the cells are intact cells. Preferably, the polyglycolic acid comprises less than 10% of the cross-sectional area of the construct. More preferably, the polyglycolic acid comprises less than 5% of the cross-sectional area of the construct. Most preferably, the polyglycolic acid comprises less than 3% of the cross-sectional area of the construct.

The extracellular matrix protein construct can comprise a burst pressure of greater than 2000 mm Hg. The construct can comprise a suture strength of greater than 120 g. The inner diameter of the tubular construct can be about 3 mm to about 20 mm. The thickness of the tubular construct can be greater than about 200 micrometers at the thinnest portion of the construct. The construct can be impermeable to fluid. Preferably, the construct is impermeable to fluid leakage up to at least 200 mm Hg, at least 300 mm Hg, or at least 400 mm Hg. The length of the construct is about 1 cm to about 100 cm. Preferably, the length of the construct is about 10 cm to about 40 cm.

The extracellular matrix proteins can comprise hydroxyproline, vitronectin, fibronectin and collagen type I, collagen type III, collagen type IV, collagen VI, collagen XI, collagen XII, fibrillin I, tenascin, decorin, byglycan, versican and asporin. Preferably, the extracellular matrix proteins can comprise hydroxyproline at >40 µg/mg dry weight. In some embodiment, the construct does not comprise elastin, MAGP1 and/or MAGP2. Preferably, the extracellular matrix proteins are produced from allogeneic, autologous or xenogeneic cells to the intended recipient of the construct. Preferably, the extracellular matrix proteins are, in part, oriented circumferentially around the tubular construct.

The construct can comprise less than 300 ng/cm of beta-actin. The construct can comprise less than 3% dry weight of lipids. The construct can comprise trace amounts or no detectable amounts of double stranded genomic DNA. Preferably, the amount of DNA is as determined by gel electrophoresis.

The construct induces little to no calcification upon implantation in vivo. Preferably, the construct induces less than 1% calcification within 6 months of implantation. More preferably, the construct induces less than 1% calcification within 12 months of implantation. Most preferably, the construct produces no calcification within 12 months of implantation.

The construct induces little to no immune response upon implantation in vivo. Preferably, when implanted as a vascular graft, the construct induces less than 1 mm of intimal hyperplasia thickening in native vasculature and in the graft at anastomoses with the construct at 6 months of implantation. More preferably, the construct induces less than 0.25 mm of intimal hyperplasia thickening in native vasculature at anastomoses with the construct at 6 months of implantation.

The construct does not dilate greater than 50% beyond its implant diameter after implantation. The construct may be stored at about 2° to about 30° C. Preferably, storage at about 2° to about 30° C. is tolerated for at least 3 months. Most preferably, storage at about 2° to about 30° C. is tolerated for at least 12 months.

The present invention also provides methods of producing a tubular construct comprising (a) providing a tubular biodegradable polyglycolic acid construct, (b) seeding human cells at passage 6 or less on the tubular biodegradable polyglycolic acid construct, (c) culturing the cells under conditions such that the cells secrete extracellular matrix proteins on the tubular biodegradable polyglycolic acid construct, (d) decellularizing the construct in step (c) such that the construct is substantially acellular comprising less than 5% cells and wherein the construct is immune- and calcification-resistant, and (e) degrading the polyglycolic acid construct in step (c) such that the polyglycolic acid comprises less than 33% of the cross-sectional area of said construct, thereby producing a decellularized tubular construct. The present invention also provides a decellularized tubular construct formed by the methods described herein.

Preferably, the construct is substantially acellular comprising less than 2% cells, less than 1% cells or contains no cells. Preferably, the cells are intact cells. The cells can be allogeneic, autologous or xenogeneic to the intended recipient. Preferably the cells are allogeneic.

The cells are obtained from a single donor or obtained from a cell bank, wherein the cells in the cell bank are pooled from a plurality of donors. Preferably, the cells are obtained from a cell bank of a plurality of donors. Preferably, each donor is less than 50 years of age and/or has not been diagnosed with a vascular disease. The cells can be isolated from human aorta. Preferably, the cells can be isolated from human thoracic aorta. More preferably, the cells comprise smooth muscle cells.

Preferably, the cells are at passage 5 or less, at passage 4 or less, at passage 3 or less. The cells can be cultured for a culture period of about six to about 11 weeks. The cells can be cultured in medium comprising high glucose, insulin, bFGF and/or EGF. Preferably, the medium comprises DMEM. Preferably, the cells are at cultured in medium comprising about 11% to about 30% human serum for the first 2-6 weeks of culture and in medium comprising about 1% to about 10% human serum for the remainder of the culture period (at least 4 weeks, at least 5 weeks). More preferably, the cells are at cultured in a bioreactor.

The cells can be at seeded onto the tubular biodegradable polyglycolic acid construct at about $0.5 \times 10^6$ cells per cm length of construct to about $2 \times 10^6$ cells per cm length of construct. Preferably, each cell of the seeded cells, or each cell's collective progeny, produces greater than 1 ng of hydroxyproline over 9 weeks in culture.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE DRAWINGS

FIG. 2A shows a human cell-derived 6 mm construct (g) implanted between the axillary artery (a) and the brachial vein (v) in a baboon model. FIG. 2B shows an arteriovenous graft (g) first accessed with 16 G needles at 4 weeks post implant. FIG. 2C shows a representative explant angiogram demonstrating a patent graft (g). The arterial anastomosis (aa), venous anastomosis (va), and brachial vein (v) are denoted. FIG. 2E shows a canine cell-derived 3 mm construct (g) as a carotid bypass, with clips occluding the intervening carotid artery (ca), at implant. FIG. 2E shows a representative angiogram demonstrating patency with no luminal narrowing at one year. FIG. 2F shows a canine cell-derived 3 mm-diameter construct (g) implanted on the heart. FIG. 2G shows a CT scan demonstrating a patent graft (g) with no dilatation at 1 month.

FIG. 3A shows a drawing of a 6 mm-diameter decellularized human extracellular matrix protein construct before implant. FIG. 3B shows a representative decellularized construct demonstrating the presence of no cells in H&E stained sections (arrow points to residual PGA), and the porous structure typical of a decellularized construct. FIG. 3C shows a decellularized construct stained strongly and diffusely for Collagen Type I. FIG. 3D shows a decellularized construct stained for organized Collagen Type III. FIG. 3E shows a decellularized construct stained for organized Fibronectin. FIG. 3F shows a decellularized construct stained for organized Vitronectin. Areas staining positive for extracellular matrix proteins are noted with open arrowheads. In 3C-F, circumferential alignment of extracellular matrix proteins is apparent. Note that DAB staining masks the porous structure in Fig. C-F. Scale bars, 100 µm.

FIG. 4A shows a 6 mm-diameter human extracellular matrix protein construct explanted from the baboon model at 6 months demonstrating formation of a loose external adventitial-like layer (g: graft, a: "adventitia"). FIG. 4B shows a 4 mm-diameter canine construct explanted from carotid bypass model at 1 year (arrow points to anastomotic suture line). FIG. 4C is a Movat's stain illustrating elastin (black) in a 6-month baboon explant. FIG. 4D is an H&E stain of a 6 mm-diameter baboon explant at 6 months showing cells densely populating graft walls close to the arterial anastomosis (arrowheads point to stained cells in D-I). FIG. 4E shows that after 6 months in the baboon model, α-smooth muscle actin positive cells (brown) populated the construct wall near anastomotic sites (note: concentrated staining was observed below the luminal surface, but cells on the lumen were not actin-positive). FIG. 4F shows that these cells started to infiltrate the construct midgraft from surrounding adventitial-like tissue (arrows define depths of graft walls in FIG. 4F-4H). FIG. 4G shows that in the canine model, α-smooth muscle actin positive cells (green) were observed infiltrating into midgraft sections of canine carotid artery bypass grafts from surrounding adventitial-like tissue at 1 month. FIG. 4H shows that at one year, actin-positive cells were observed through the depth of canine graft walls. FIG. 4I shows a construct explanted from a baboon demonstrating positive staining for von Willebrand Factor in luminal cells (section near anastomosis shown). Scale bars, 100 μm.

FIG. 5A shows that intradermal injections of homogenized graft material and PBS (negative control) in baboons at 4 weeks post implantation displayed no visible induration or redness. FIG. 5B is a graph illustrating representative proliferation of T-cells isolated at implant (week 0) and 24 weeks after implant, after exposure to segments of PTFE (negative control; not implanted) and constructs (labeled TEVG), demonstrated that grafts are immunologically tolerated. FIG. 5C is a photograph of H&E staining showing a large population of infiltrated cells in anastomotic sections of constructs at 6 months in the baboon. FIG. 5D shows that only a sparse population of cells in anastomotic sections stain positive for CD3 (T-lymphocyte marker) at 6 months in the baboon. FIG. 5E shows that only a sparse population of cells in anastomotic sections stain positive for CD20 (B-lymphocyte marker) at 6 months in the baboon. FIG. 5F shows the absence of calcification (lack of red color) in alizarin red stain in a human constructs explanted from the baboon model at 6 months. Arrows point to stained cells. Scale bars, 300 μm.

FIG. 7A illustrates uniform PGA density. FIG. 7B illustrates non-uniform PGA density, with low and high density regions. FIG. 7C illustrates a tubular polymeric construct with a uniformly entangled seam which matches the overall density of the tubular construct and a PET anchor. FIG. 7D illustrates a tubular polymeric construct where the seam is poorly entangled and having variable density (high and low density regions).

FIG. 8A illustrates venous anastomosis of an extracellular matrix protein construct of the invention. FIG. 8B illustrates substantial venous intimal hyperplasia adjacent to a PTFE graft.

FIG. 9A shows that the conduit supports end-to-end and end-to-side anastomoses with ureters, and is tunneled in the retroperitoneal plane. At the skin, the conduit forms a stoma with the skin. FIG. 9B shows the extracellular matrix protein conduit skin stoma, with diverted urine. A stent, which is routinely used in the clinic to maintain an open conduit during the surgical healing process, is shown inserted into the extracellular matrix protein conduit through the skin stoma. FIG. 9C shows an ostomy bag collecting urine that is draining from the stoma of the urinary diversion conduit. FIG. 9D shows the conduit after 28 days of exposure to concentrated urine. FIG. 9E shows that after 4 weeks of exposure to concentrated urine, conduits resisted crystallization, and remained physically and mechanically intact.

DETAILED DESCRIPTION OF THE INVENTION

Figure 1:
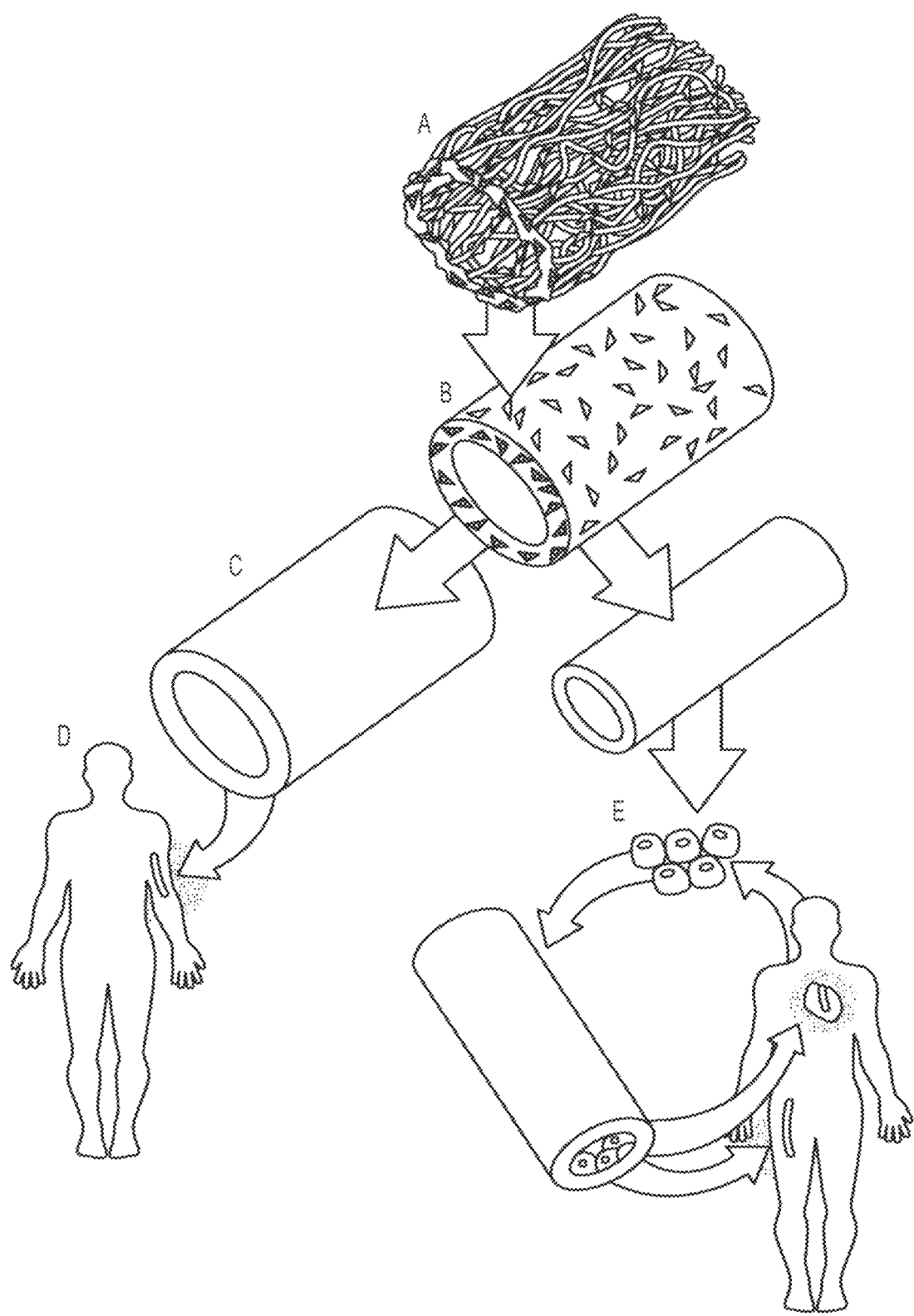
FIG. 1 is a schematic illustration of the approach used to produce readily available extracellular matrix protein constructs. Each constructs is generated in the laboratory by (step A) culturing human cells on a polymer scaffold that degrades as the cells produce extracellular matrix proteins to form (step B) a tissue. Cellular material is then removed, leaving (step C) an extracellular matrix construct, which may be refrigerated or stored at room temperature, or by some other storage means until the time of patient need. Cell-derived extracellular matrix protein constructs may be implanted without cells (step D, diameters ≥6 mm), or (step E) seeded with recipient endothelial cells for small diameter (3-4 mm) applications.

The present invention provides a construct including a biodegradable polymeric scaffold, wherein the density of the polymeric material is about 45 mg/cc to about 75 mg/cc and said density is uniform across the entire tubular scaffold. Uniform as used herein is defined as no more than 30%, no more than 15%, no more than 10%, no more than 5%, no more than 4%, no more than 3%, no more than 2%, no more than 1% variability in density over 100% of the surface area of the scaffold. The scaffold may be in any shape known in the art. Preferably, the scaffold is tubular. Any synthetic, biodegradable, polymeric material known in the art may be utilized. Preferably, the polymeric material is polyglycolic acid. The scaffold may be in any form known in the art. Preferably, the scaffold is felt. These constructs are referred to interchangeably herein as "polymeric constructs", "polymeric scaffolds", "polyglycolic acid (PGA) constructs" or "polyglycolic acid (PGA) scaffolds"

The length of the tubular biodegradable polyglycolic acid scaffold can be about 1 cm to about 100 cm. Preferably, the length of the tubular biodegradable polyglycolic acid scaffold can be about 10 cm to about 40 cm. More preferably, the length can be at least at least 5, at least 10, at least 12, at least 13, at least 14, at least 20, at least 25, or at least 30 cm in length. The inner diameter of the tubular biodegradable polyglycolic acid scaffold can be equal to or greater than about 3 mm. Preferably, the inner diameter of the tubular biodegradable polyglycolic acid scaffold can be about 3 mm to about 20 mm, such at least 3 mm, at least 4 mm, at least 5 mm, or any integer up to about 20 mm.

The thickness of the polyglycolic acid can be about 0.8 to about 1.5 mm and said thickness is uniform across the tubular scaffold. Preferably, the polyglycolic acid can be about 0.8 to about 1.2 mm. The thickness of the fibers within the polyglycolic acid can be about 5 to about 20 μm. The porosity of the polyglycolic acid can be about 90% to about 98%.

The constructs of the present invention can further include non-biodegradable polyethylene terephthalate supports at each end of the tubular biodegradable polyglycolic acid scaffold. The non-biodegradable polyethylene terephthalate supports can be attached to the tubular biodegradable polyglycolic acid scaffold by any means known in the art. Preferably, the polyethylene terephthalate supports are attached via sutures. The porosity of the polyethylene terephthalate can be $\geq 200$ cc/min/cm$^2$. The tubular biodegradable polyglycolic acid scaffold and the non-biodegradable polyethylene terephthalate supports can permit the attachment and growth of cells. Alternatively, other non-degradable polymers can be used as supports at each end of the tubular scaffold.

The constructs of the present invention are substantially free of heavy metal contaminants. Preferably, the construct includes only trace amounts of heavy metal contaminants selected from the group consisting of: aluminum, barium, calcium, iodine, lanthanum, magnesium, nickel, potassium and zinc. Aluminum can be present in an amount from about 1.5 ppm to about 5 ppm. Barium can be present in an amount from about 0.03 ppm to about 0.06 ppm. Calcium can be present in an amount from about 10 ppm to about 4 ppm. Iodine can be present in an amount from about 0.1 ppm to about 0.04 ppm. Lanthanum can be present in an amount from about 0.05 ppm to about 0.3 ppm. Magnesium can be present in an amount from about 0.5 ppm to about 3.5 ppm. Nickel can be present in an amount from about 0.1 ppm to about 1 ppm. Potassium can be present in an amount from about 5 ppm to about 40 ppm. Zinc can be present in an amount from about 1 ppm to about 5 ppm.

The constructs of the present invention can further include extracellular matrix proteins within, and around, the biodegradable polyglycolic acid scaffold. Preferably, the thickness of the extracellular matrix proteins is greater than about 200 micrometers at the thinnest portion of the construct.

The present invention also provides methods of producing a tubular polyglycolic acid construct including (a) providing a biodegradable polyglycolic acid sheet, wherein the density of the polyglycolic acid is about 45 mg/cc to about 75 mg/cc and the thickness of the polyglycolic acid sheet is about 0.8 to about 1.2 mm, (b) wrapping the polyglycolic acid sheet around a mandrel such that opposite edges of the polyglycolic acid sheet meet at an interface; (c) pulling polyglycolic acid fibers from each opposing edge of the sheet across the interface, and (d) forming a seam by entangling said pulled polyglycolic acid fibers from one side of the interface with the polyglycolic acid fibers on the opposite side of the interface, wherein the density of the polyglycolic acid at the seam is about 45 mg/cc to about 75 mg/cc and the thickness of the polyglycolic acid at the seam is about 0.8 to about 1.5 mm, thereby producing a tubular biodegradable polyglycolic acid construct with a uniform polyglycolic acid density. The present invention also provides a tubular biodegradable polyglycolic acid construct formed by the methods described herein.

The mandrel can comprise any material known in the art. Preferably, the mandrel comprises a gas permeable, silicone tube.

The entangling step may be performed by any method known in the art which permits the seam to remain intact in subsequent treatment steps. Preferably, entangling is performed with a felting needle.

The methods of the present invention can further include, treating the tubular construct to remove heavy metal contaminants. Preferably, the tubular construct is treated with one or more non-polar solvents and treated with at least one primary alcohol, such as ethanol. Preferably, the seam remains intact following said treatment. This treatment may also be performed on the biodegradable scaffold prior to formation of a tube.

The methods of the present invention can further include, treating the tubular construct to increase the rate of polyglycolic acid degradation and/or increase the wettability of the polyglycolic acid. Preferably, the tubular construct is treated with a strong base. More preferably, the strong base is 1M NaOH. Preferably, the seam remains intact following said treatment. This treatment may also be performed on the biodegradable scaffold prior to formation of a tube.

The methods of the present invention can further include, attaching non-biodegradable polyethylene terephthalate supports at end of the tubular biodegradable polyglycolic acid scaffold. These supports may be attached prior to or after other treatments of the tubular construct.

The present invention also provides a tubular construct comprising extracellular matrix proteins and a polymeric material having an internal diameter of ≥3 mm, wherein the construct is immune and calcification resistant, wherein the polymeric material comprises less than 33% of the cross-sectional area of said construct and wherein the construct is substantially acellular comprising less than 5% cells. Stimulation of immunity is determined, in some embodiments, by reaction to intradermal injections of construct material into the recipient, at 48 hours after injection. Preferably, the polymeric material is polyglycolic acid. These constructs are referred to interchangeably herein as "extracellular matrix protein constructs", "decellularized constructs"; or may be referred to as "grafts", "conduits" or "vessels" depending upon in vivo usage.

The extracellular matrix protein constructs can be used in a number of anatomical locations and disease situations. The construct can be selected from the group consisting of an arteriovenous graft, a coronary graft, peripheral artery bypass conduit, fallopian tube replacement, and a urinary conduit. For example, extracellular matrix protein constructs are useful as arteriovenous grafts in patients undergoing hemodialysis; as coronary grafts in bypassing a blockage in patients, to bypass a diseased peripheral artery in a patient with peripheral artery disease (PAD) or as a urinary conduit. The diameter and length of the extracellular matrix protein constructs will vary for these different uses as will the surgical attachment points. For example, a coronary graft will attach to coronary artery, a peripheral artery graft will attach to a peripheral artery and a urinary conduit will typically connect the ureter(s) to the skin to form a stoma.

Every year in the US, approximately 10,000 patients undergo cystectomy, and require a urinary conduit to drain urine outside the body (Healthcare Cost and Utilization Project (2007). N.I.S.). In almost all cases, bowel is harvested from the patient to form either an incontinent urinary diversion, or a continent urinary diversion that is catheterized intermittently to drain urine through a continent stoma (Konety B R, Joyce G F, Wise M (2007) Bladder and upper tract urothelial cancer. *J Urol* 177:1636-1645). Patients may suffer from complications at the bowel harvest site, including anastomotic leaks and peritonitis. In addition, ileal urinary conduits may suffer from ischemia and necrosis, which can lead to perforation, anastomotic breakdown, stoma problems, and leakage of urine from the conduit. In the long term, many patients suffer from chronic hyperchloremic metabolic acidosis, due to resorption of urine electrolytes through the conduit wall. Since ileal conduits harbor bacteria, patients also commonly suffer from recurrent urinary tract infections and pyelonephritis, as bacteria from the conduit infect the more proximal urinary system. Hence, there is a significant medical need for an improved method for urinary diversion that avoids many of the complications associated with the use of ileal conduits (Konety B R, Allareddy V (2007) Influence of post-cystectomy complications on cost and subsequent outcome. *J Urol* 177:280-287; Dahl D M, McDougan W S (2009) Use of intestinal segments and urinary diversion. In: Wein A J, Kavoussi L R, Novick A C (eds) *Campbell-Walsh Urology.* 9th Edn.).

Surprisingly, the extracellular matrix protein constructs of the present invention provide significant superior properties when compared to autologous ileum. For example, no resection of the patient's intestine is needed, as surgery on the bowel is completely avoided. As described herein, the urinary conduit of the present invention is pre-manufactured and stored, making it readily available to patients. Since the extracellular matrix protein construct of the present invention when used as a urinary conduit does not actively absorb its luminal contents, the risk of hyperchloremic metabolic acidosis is substantially reduced. Since the extracellular matrix protein construct of the present invention when used as a urinary conduit does not harbor intestinal flora, the risks of recurrent urinary tract infections are markedly reduced. The extracellular matrix protein construct of the present invention when used as a urinary conduit does not produce mucus, and therefore, risk of clogging the stoma is reduced when compared to the mucus-producing ileal conduit. Since the extracellular matrix protein construct of the present invention is non-living, there is essentially no risk of tissue ischemia due to inadequate vasculature. Rather, host cells gradually migrate into the acellular conduit and concurrently form a microvascular network. Without ischemia, the risk of stomal stenosis is reduced. Since the extracellular matrix protein construct of the present invention can be grown at diameters ranging from 3-20 mm or greater, and with lengths of up to 100 cm, it is possible to produce urinary conduits having the dimensions most suitable for diversion of urine to the skin surface. The urinary conduit tolerates chronic exposure to urine and resists active diffusion of urine through the conduit wall.

Figure 10:
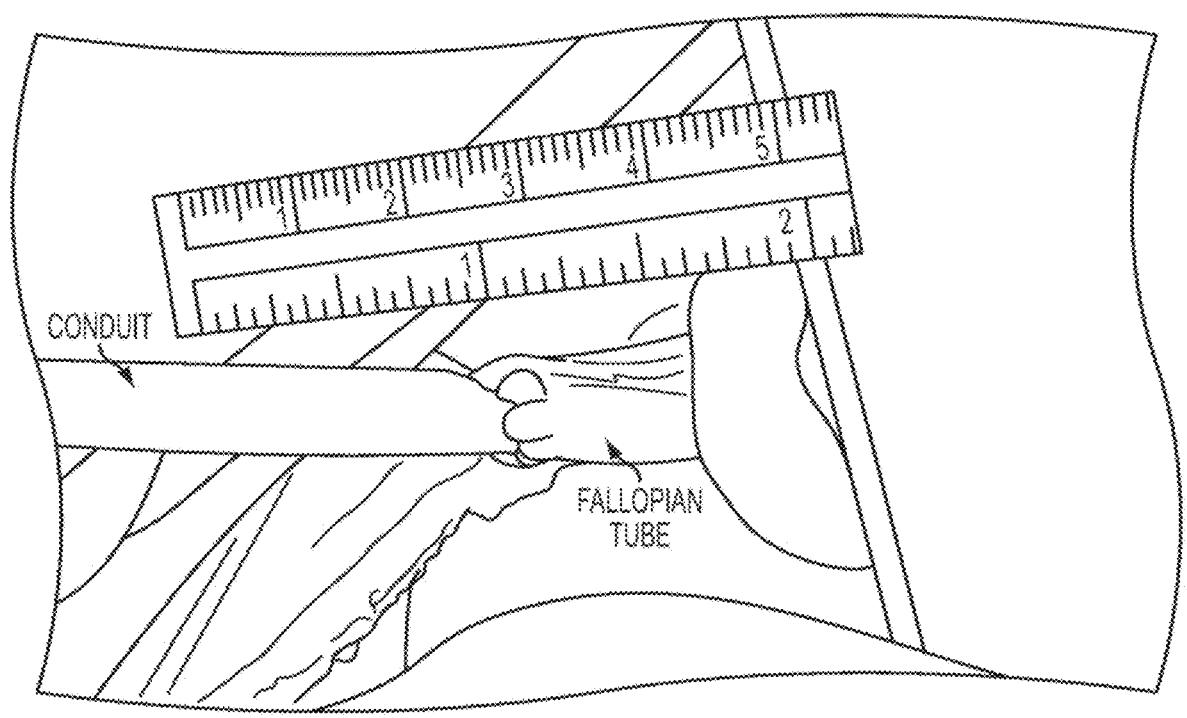
FIG. 10 is a diagram showing usage of the extracellular matrix protein constructs of the present invention as a fallopian tube conduit.

Fallopian tube scarring is a major problem that can cause infertility. Infection, such as that associated with some sexually transmitted diseases, can cause scar tissue to form in the fallopian tubes. Scar tissue, in turn, blocks or damages the fallopian tube. A blocked fallopian tube prevents fertilization of the egg, and a damaged fallopian tube can lead to ectopic pregnancies. In the United States, more than 750,000 women experience an episode of acute pelvic inflammatory disease each year, and 10-15% of these women become infertile as a result (Pelvic Inflammatory Disease (PID)—CDC Fact Sheet, National Center for HIV/AIDS, Viral Hepatitis, STD, and TB Prevention, Division of STD Prevention, September 2011). Fallopian tube cancer affects approximately 550 women in the United States each year (Vapiwala, N, and Hill-Kayser, C, *Fallopian Tube Cancer: The Basics*, OncoLink, Abramson Cancer Center of the University of Pennsylvania, 2010). FIG. 10 shows, in a porcine model, that the extracellular matrix protein constructs of the present invention can be sewn an end-to-end anastomosis to replace an excised segment of fallopian tube.

The tubular construct is decellularized such that it is substantially acellular such that the construct is immune-resistant and/or calcification resistant. Preferably, the construct is substantially acellular comprising less than 2% cells, less than 1% cells or contains no cells. The cells are intact cells. The cells can be living cells or dead cells.

The tubular construct is treated to minimize the amount of polymeric material present. Preferably, the polymeric material is polyglycolic acid. The polymeric material may degrade or be removed such that less than 50%, less than 45%, less than 40%, less than 35%, less than 33%, less than 30%, less than 25%, less than 20%, less than 15%, less than 10%, less than 5%, less than 3%, or less than 1% of the cross-sectional area of the tissue comprises the synthetic polymeric material. Calculation of the cross-sectional area does not include the lumen.

The length and diameter of the extracellular matrix protein construct may vary with the anatomical application desired. The length of the extracellular matrix protein construct acid scaffold can be about 1 cm to about 100 cm. Preferably, the length is about 10 cm to about 40 cm. More preferably, the length can be at least at least 5, at least 10, at least 12, at least 13, at least 14, at least 20, at least 25, or at least 30 cm in length. The inner diameter of extracellular matrix protein construct can be equal to or greater than about 3 mm. Preferably, the inner diameter is be about 3 mm to about 8 mm, such at least 3, at least 4, at least 5, at least 6, at least 7, or at least 8 mm. More preferably, the inner diameter can be about 3 mm to about 20 mm.

Surprisingly, the extracellular matrix protein construct can comprise a burst pressure of at least 600 mm, at least 700 mm, at least 800 mm, at least 900 mm, at least 1000, at least 1100 mm, at least 1200 mm, at least 1300 mm, at least 1400 mm, at least 1500 mm, at least 1600 mm, at least 1700, at least 1800 mm, at least 1900 mm or at least 2000 mm Hg. Burst pressure can be measured by any means known in the art; for example, by inflating the construct with a fluid at gradually increasing pressures, until the construct either ruptures or forms a discrete hold. Preferably, the construct has a burst strength greater than 2000 mm Hg. Equally surprising, the construct can comprise a suture strength of greater than 60 g, 70 g, 80 g, 90 g or 120 g. Preferably, the construct has a suture strength greater than 120 g. Suture strength can be measured by any means known in the art; for example, by inserting a 6-0 suture through the construct at a distance of 2 mm from the edge of the construct. The thickness of the tubular construct can be greater than about 200 micrometers at the thinnest portion of the construct. The construct can be impermeable to fluid. The fluid can be saline or a biological fluid such as blood or urine. Impermeable to fluid is defined as the absence of net fluid flow out of the construct after filling with fluid at atmospheric pressure, at 200 mm Hg, at 300 mm Hg or 400 mm Hg. Preferably, the construct is impermeable to fluid leakage up to at least 200 mm Hg, at least 300 mm Hg or at least 400 mm Hg. Given that normal pressures in blood vessels do not exceed 120 mm Hg, and that severe Stage 4 blood pressures in hypertension reach a maximum of up to 230 mm Hg, the extracellular matrix protein constructs provided herein resist leakage and weeping in both healthy and sick patients. Given that ureteral pressures are approximately 30 mmHg, this construct also resists leakage of urine during use as a urinary conduit. Without being bound by any theories, the extracellular matrix protein constructs provided herein resist leakage and weeping because the extracellular matrix proteins (e.g., collagen) is closely packed in the constructs, with a density of 856±221 micrograms hydroxyproline per $cm^2$ of construct material.

The extracellular matrix proteins can comprise hydroxyproline, vitronectin, fibronectin and collagen type I, collagen type III, collagen type IV, collagen VI, collagen XI, collagen XII, fibrillin I, tenascin, decorin, byglycan, versican and asporin. Preferably, the extracellular matrix proteins can comprise hydroxyproline at >40 µg/mg dry weight. Preferably, the extracellular matrix proteins are produced from allogeneic, autologous or xenogeneic cells. Preferably, the extracellular matrix proteins are, in part, oriented circumferentially around the tubular construct. Circumferential orientation of extracellular matrix proteins provides an "anchor" for sutures. The arrows in FIG. 3 highlight the circumferential orientation of fibers. In contrast, having a predominantly axial orientation of extracellular matrix does not provide the sutures with a structure to anchor onto; rather the suture would slip through axially aligned fibers.

The construct can comprise less than 300 ng/cm of beta-actin. Preferably, the construct comprises <150 ng/cm of beta-actin. The amount of beta-actin can be determined by any means known in the art; for example, by ELISA assay. The construct can comprise less than 3% dry weight of lipids. The amount of lipid can be determined by any means known in the art; for example, by gas chromatography-mass spectrometry. The construct can comprise trace amounts or no detectable amounts of double stranded genomic DNA. Preferably, the amount of DNA is as determined by gel electrophoresis.

The construct induces little to no calcification upon implantation in vivo. Preferably, the construct induces less than 1% calcification within 6 weeks, within 3 months, within 6 months, within 9 months, or 12 months of implantation. More preferably, the construct induces less than 0.5% calcification within 6 weeks, within 3 months, within 6 months, within 9 months, or 12 months of implantation. Most preferably, the construct produces no calcification within 6 weeks, within 3 months, within 6 months, within 9 months, or 12 months of implantation. Calcification can be determined by any means known in the art; for example, calcification is measured by percent area of the construct that on histologic sectioning stains positive for calcium, using a histochemical stain such as alizarin red stain.

The construct is immune-resistant such that the construct induces little to no immune response upon implantation in vivo, as defined by wheal formation and redness at 48 hours after intracutaneous injection of graft material particles into the recipient. Preferably, the construct induces less than 1 mm of intimal hyperplasia thickening in native vasculature at anastomoses with the construct at 3 months, 6 months, 9 months, or 12 months of implantation, when implanted as a vascular graft. More preferably, the construct induces less than 1, 0.75, 0.5, 0.4, 0.3, or 0.25 mm of intimal hyperplasia thickening in native vasculature at anastomoses with the construct at 6 months of implantation.

Surprisingly, the extracellular matrix protein constructs do not dilate greater than 50, %, greater than 40%, greater than 30%, or greater than 20% beyond their diameter at time of implant. This is very beneficial in vivo. Also surprisingly, the extracellular matrix protein constructs are very storage stable, and can be stored before or after decellularization. The construct may be stored at about 2° to about 30° C. for at least 1, 2, 3, 4, 6, 8, 12, 18, or 24 months without comprising their integrity and implantability. The integrity of the constructs can be assessed by any means know in the art; for example, as assessed by retained suture retention strength of at least 80% of starting value. The constructs can be stored in any suitable physiological buffer known in the art. The buffer may include protease inhibitors, or ion chelators. This is very beneficial as the extracellular matrix protein constructs are readily available (minimal or no wait time) for in vivo use.

The present invention also provides methods of producing a tubular construct comprising (a) providing a tubular biodegradable polyglycolic acid construct, (b) seeding human cells at passage 6 or less on the tubular biodegradable polyglycolic acid construct, (c) culturing the cells under conditions such that the cells secrete extracellular matrix proteins on the tubular biodegradable polyglycolic acid construct, (d) decellularizing the construct in step (c) such that the construct is substantially acellular comprising less than 5% cells and wherein the construct is immune and calcification resistant, and (e) degrading the polyglycolic acid construct in step (c) such that the polyglycolic acid comprises less than 33% of the cross-sectional area of said construct, thereby producing a decellularized tubular construct. The present invention also provides a decellularized tubular construct formed by the methods described herein.

The tubular construct is decellularized such that it is substantially acellular such that the construct is immune-resistant and/or calcification resistant. Preferably, the construct is substantially acellular comprising less than 2% cells. More preferably, the construct is substantially acellular comprising less than 1% cells. Most preferably, the construct contains no cells. Thus, in the decellularization step greater than 25%, greater than 40%, greater than 50%, greater than 75%, greater than 85%, greater than 90%, greater than 95%, greater than 98%, or greater than 99% of the cells seeded onto the tubular biodegradable polyglycolic acid construct are removed. The cells can be allogeneic, autologous or xenogeneic to the host to which the construct will be implanted. Preferably the cells are allogeneic.

The cells are obtained from a single donor or obtained from a cell bank, wherein the cells in the cell bank are pooled from a plurality of donors. Preferably, the cells are obtained from a cell bank of a plurality of donors. Preferably, each donor is less than 50 years of age and/or has not been diagnosed with a vascular disease. The cells can be isolated from human aorta, femoral artery, iliac artery, carotid artery, radial artery, ureter, bladder wall or skin. Preferably, the cells are isolated from human aorta. More preferably, the cells are isolated from human thoracic aorta. The cells can comprise smooth muscle cells, mesenchymal cells, fibroblasts, fibrocytes, and/or endothelial cells. Preferably, the cells comprise smooth muscle cells.

The seeded cells are low passage cells, having been passaged less than 10, less than 5, less than 5, less than 4, less than 3, or less than 2 times. Preferably, the cells are at passage 3 or less. The cells can be cultured for a culture period of about six to about 11 weeks. The polymeric scaffold may be in any form during the phase of culturing. It can be in the ultimate shape, or it can be shaped after the phase of culturing. Preferably, the scaffold is tubular. Alternatively, the scaffold is shaped into a tubular form after the culturing. Culturing of the cells can be performed using any conventional medium and apparatus, taking into account nutritional, oxygenation, temperature, mechanical, and pressure conditions. The medium may optionally comprise bovine serum, porcine serum, ovine serum, equine serum, or human serum. Such sera may provide growth factors and known or unknown components for improving properties of the culturing process. As the cells grow in culture on the scaffold, they secrete collagenous extracellular matrix. Preferably, the cells are at cultured in medium comprising 20% human serum for the first 2-6 weeks of culture and 10% human serum for the remainder of the culture period. More preferably, the cells are at cultured in a bioreactor.

The cells can be at seeded onto the tubular biodegradable polyglycolic acid construct at about $0.5 \times 10^6$ cells per cm length of construct to about $2 \times 10^6$ cells per cm length of construct. Preferably, each cell of the seeded cells, or each cell's collective progeny, produces greater than 1 ng of hydroxyproline over 9 weeks in culture.

The methods of the present invention can further include: prior to implantation in a patient, seeding cells on the decellularized tubular construct. The cells can include smooth muscle cells or endothelial cells. Preferably, the cells are endothelial cells. The cells can be allogeneic or autologous cells. Preferably, the cells are autologous cells. Most preferably, the cells are autologous endothelial cells.

Decellularized extracellular matrix protein constructs have several advantages over decellularized human cadaveric vessels. First, cadaveric human vasculature has small branches that must be ligated, whereas engineered tissues consist of a tube without branches. Second, decellularized extracellular matrix protein constructs have a loose tissue structure without layers of lamellar elastin. This loose structure allows decellularization solutions to readily permeate engineered tissues to remove cellular material without excessive exposure that may damage extracellular matrix integrity, and also may improve cellular repopulation in vivo. Thirdly, using a decellularized extracellular matrix protein constructs approach maximizes the impact of healthy tissue donors by allowing production of a large number of grafts per donor, whereas a decellularized cadaveric vascular graft approach has limited amounts of available vascular tissue per donor with diameters that are appropriate for common cardiovascular surgical procedures. Extracellular matrix protein constructs can be created in a variety of diameters that can more suitably match bypassed native arterial vasculature. In contrast, decellularized human cadaveric vessels cannot be created for a particular diameter, and size mismatch between the small native vessel and large bypass graft can occur, potentially resulting in diminished patency rates.

Constructs can be decellularized using any means known in the art; for example, as described previously (Dahl, et al., *Cell Transplantation* 12, 659-666 (2003)). One preferred decellularization solution comprises phosphate buffered saline (PBS) with 0.12M sodium hydroxide, 1M sodium chloride, and 25 mM EDTA, containing either 8 mM CHAPS or 0.07-1.8 mM SDS. Another preferred decellularization solution does not comprise SDS. The decellularization methods of the present invention may include a benzonase step to digest DNA. Preferably, the benzonase step includes a solution comprising 2 U/mL Benzonase, 47 mM Tris, 1.4 mM magnesium chloride, and 19 mM sodium chloride, at pH 8.0.

The presence of sparse residual PGA fragments in extracellular matrix protein constructs at the time of implant is not of concern, as PGA is an FDA-approved degradable suture material with breakdown products that are readily metabolized. Further, PGA has been used as a vascular graft component without any known negative effects on vascular remodeling (Shin'oka, et al., *J Thorac Cardiovasc Surg* 129, 1330-1338 (2005)). The human cell-derived grafts produced in this study were an order of magnitude stronger than those described in previous reports that also used PGA as a support for tissue creation (Poh, et al., *Lancet* 365, 2122-2124 (2005); McKee, et al., *EMBO Rep* 4, 633-638 (2003)). However, it is important to note that these prior reports utilized human venous cells or commercially available human aorta cells at high passage (Poh, et al., *Lancet* 365, 2122-2124 (2005); McKee, et al., *EMBO Rep* 4, 633-638 (2003)). In previous reports, use of dense PGA sutures to sew sheets of PGA into tubes left a substantial amount of residual PGA in extracellular matrix protein constructs, which diminished extracellular matrix protein construct strengths (Dahl, et al., *Ann Biomed Eng* 35, 348-355 (2007)).

In large diameter applications, such as above-the-knee peripheral bypass surgery and hemodialysis access, PTFE vascular grafts function well enough to warrant routine clinical use (Harris, et al., *J Vasc Surg* 33, 528-532 (2001)). Therefore, large diameter extracellular matrix protein constructs can be utilized without luminal EC seeding. However, for small diameter applications, it has been extremely difficult to find a functional vascular graft other than the patient's own vasculature (Harris, et al., *J Vasc Surg* 33, 528-532 (2001)), which is highly compliant (Table 3) and contains ECs. To minimize risk of graft occlusion, ECs were seeded onto extracellular matrix protein constructs prior to implant in the small diameter peripheral and coronary settings to provide an antithrombogenic luminal surface. ECs were isolated from peripheral arteries or veins of dogs prior to undergoing bypass with extracellular matrix protein constructs. This is similar to peripheral vein harvest approaches previously reported for isolation of ECs for vascular graft seeding (McAllister, et al., *Lancet* 373, 1440-1446 (2009); Deutsch, et al., *J Vasc Surg* 49, 352-362 (2009)). Autologous ECs could also be isolated more rapidly from adipose tissue (Arts, et al., *Lab Invest* 81, 1461-1465 (2001)) or circulating blood (Kalka, et al., *Proc Nat Acad Sci* 97, 3422-3427 (2000); Hill, et al., *New Eng J Med* 348, 593-600 (2003)), which could reduce the patient wait time for endothelialization from weeks to days or possibly even to hours.

The observed patency rate of 83% for small diameter extracellular matrix protein constructs with poor luminal EC coverage suggests that complete luminal EC coverage prior to implant is not be required for graft function in the setting of systemic anti-platelet therapy throughout the duration of implantation. Poor EC coverage at implant is also observed in saphenous vein grafts, which are often denuded of endothelium during graft isolation (Roubos, et al., *Circulation* 92, 31-36 (1995)). It is possible that the presence of sparse ECs at the time of implant aids in maintaining patency in vivo, either by supplying sufficient release of anti-thrombogenic signals or by aiding in recruitment of recipient ECs to the extracellular matrix protein construct luminal surface (Lee, et al., *Circulation* 114, 150-159 (2006)). On the other hand, extracellular matrix protein constructs may be less thrombogenic than other, synthetic vascular graft materials and may function without ECs on the luminal surface at the time of implant.

The functional effects of immunogenicity (intimal hyperplasia, aneurysmal dilatation, or calcification in the long term (Sclafani, et al., *Arch Facial Plast Surg* 2, 130-136 (2000); Mitchell and Libby, *Circ Res* 100, 967-978 (2007); Yankah and Wottge, *J Card Surg* 12, 86-92 (1997))) were not observed in baboon or canine studies, demonstrating that the disclosed tissue engineered vascular grafts were non-immunogenic. In contrast, discordant xenogenic extracellular matrix proteins and allogeneic cells (found in bovine vascular xenografts and human cadaveric cryopreserved vascular allografts, respectively) trigger immunological responses and their functional side-effects (Allaire, et al., *Surgery* 122, 73-81 (1997); Carpenter, and Tomaszewski, *J Vasc Surg* 27, 492-499 (1998)). Extracellular matrix protein constructs resisted intimal hyperplasia formation in long-term implants. Extracellular matrix protein constructs demonstrated less neointimal hyperplasia at 6 months as arteriovenous grafts than PTFE at 1 month as arterial bypass grafts (Lumsden, et al., *J Vasc Surg* 24, 825-833 (1996)), which is encouraging given that arteriovenous grafts typically trigger more substantial intimal thickening than do arterial bypass grafts. Given that end-to-side carotid artery bypass has been described as a model that results in extensive intimal hyperplasia at one month (Kapadia, et al., *J Surg Res* 148, 230-237 (2008)), the absence of intimal hyperplasia at one year in the canine peripheral bypass studies is surprising.

The extracellular matrix protein constructs of the present invention are available without a significant patient wait time and represent a substantial advance over completely autologous tissue engineering approaches, wherein patients must wait for long time periods for grafts to be cultured. The constructs provided herein are functional as arteriovenous conduits, and as small-caliber arterial bypasses in the peripheral (carotid) and coronary circulations. Conduits used previously in the clinic have suffered from substantial intimal hyperplasia, aneurysm, and calcification. Encouragingly, the decellularized extracellular matrix protein constructs resist substantial intimal hyperplasia, dilatation, and calcification in various large-animal models. These data support the use for the decellularized human extracellular matrix protein constructs in a range of vascular applications for patients who have no available autologous vascular conduit.

Examples are provided below to further illustrate different features of the present invention. The examples also illustrate useful methodology for practicing the invention. These examples do not limit the claimed invention.

Example 1

Figure 7A:
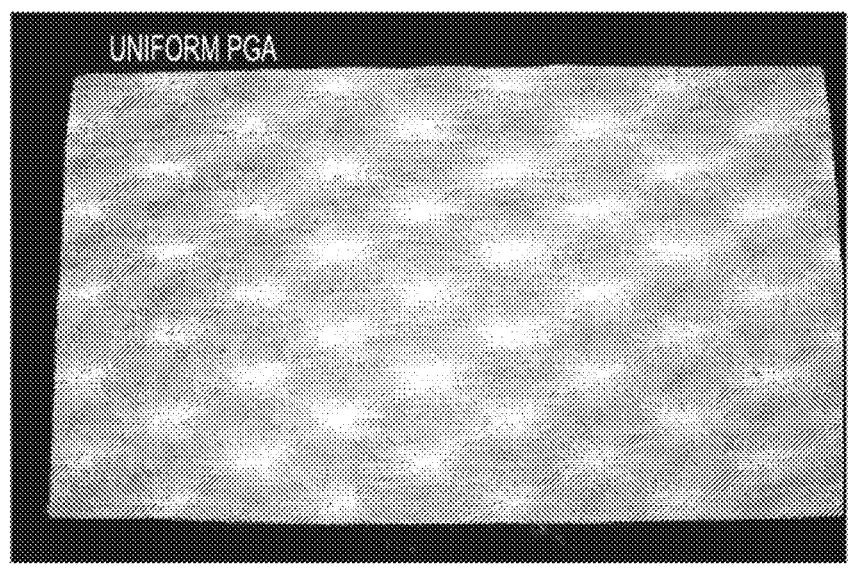
FIGS. 7A-7D is a series of photographs and diagrams showing a tubular polymeric construct.
Figure 7B:
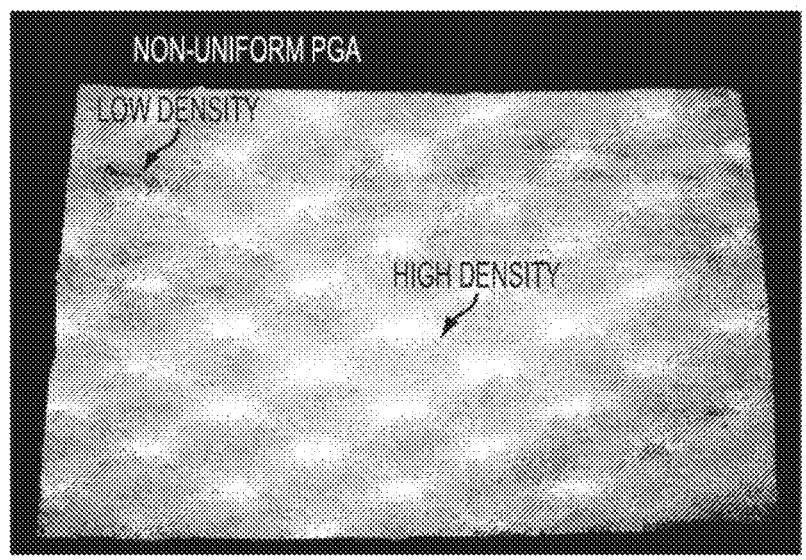

Formation of Polymeric Scaffold:
Measure proper width and length of the PGA mesh (Polyglycolic acid felt) required and cut to size. For example, 3 mm–1.35 cm×desired length; 4 mm–1.66 cm×desired length; or 6 mm–2.35 cm×desired length. PGA Mesh can be obtained from Biomedical Structures (1 mm thick, 50 mg/cc (Range 45-58), 20×30 cm). Wrap mesh around appropriately sized silicone tubing cut 10 cm longer than length of mesh. Use felting needle to pull a fiber thread from one side of the mesh to the other side to entangle PGA fibers along the seam. Repeat all along seam edge. Entangle fibers tightly against silicone tubing to create a vessel/tubular shape of the mesh. Seam should be no thicker than the rest of the tube. The seam is then secured by mending any tears, holes or thin spots throughout mesh tube The PGA is ideally 45-75 mg/cc. Low density (<45 mg/cc) regions lack a sufficient number of PGA fibers to entangle a seam without holes. Low density regions also lead to reduced cell attachment, and poor cell attachment may lead to insufficient local extracellular matrix production. High density (>75 mg/cc) PGA is associated with a greater density of PGA residuals in the final product. FIG. 7A shows a uniform-density PGA felt with density in the range of 45-75 mg/cc. FIG. 7B shows a non-uniform-density PGA felt, with regions of unacceptably low density (<45 mg/cc) that are unacceptable for use and regions of high density (>75 mg/cc) that may lead to increased residual PGA in the final product.

The fiber entangling method is used to turn PGA sheets (see PGA sheet in FIG. 7A) into tubes. The entangling method involves wrapping a strip of PGA around the silicone mandrel and meeting the edges of PGA at an interface. Thereafter, fibers of PGA from each side of the strip are pulled across the interface and inserted between fibers on the opposite side of the interface. A sufficient number of fibers must be pulled to make the "seam" strong enough to withstand subsequent scouring and surface treatment. The fibers must also be pulled in such a manner that the seam density matches that of the rest of the tubular scaffold (see FIG. 7C), so that cells will be distributed uniformly around the PGA tube and will produce a uniform tissue. If the seam is not uniform (see FIG. 7D), areas of very low density will become holes during the NaOH surface treatment process. In addition, low-density areas in the PGA seam may lead to poor local cell seeding, which may lead to a thin spot in the final graft. High density areas in the seam as shown in FIG. 7D may locally increase PGA residuals in the final product. Locally concentrated residuals of PGA in grafts may locally reduce graft strength (Dahl et al. *Ann Biomed Eng* 35 (3):348-355 (2007))

Cut polyethylene terephthalate (PET) material (Dacron® material) into 1 cm segments—about 6-7 ribs. Dacron® material can be obtained from Maquet (Rastatt, Germany; Product No. 174408, C-Code C1768, D 8 mm×L 50 cm, average porosity 260 cc/min/cm$^2$). Since the Dacron® does not gather easily, cut a small triangular wedge into Dacron cuff to fit 3 or 4 mm tubing. When the Dacron® is sutured to the mesh, close the triangular wedge to fit snuggly to the mesh and silicone tubing. Cut small slice, about 3 ribs, into Dacron® cuff to accommodate 6 mm tubing attachment to bioreactor. Using 4.0 Surgipro™ II suture (Coviden Ltd, Dublin, IRL), first sew wedge shut to fit 3 or 4 mm tube, then attach cuff to PGA mesh tube using surgeons' stitches. Sew running stitches across top of cuff to create purse string closure onto bioreactors. The tubular PGA construct may be stored or treated as described below.

Figure 7C:
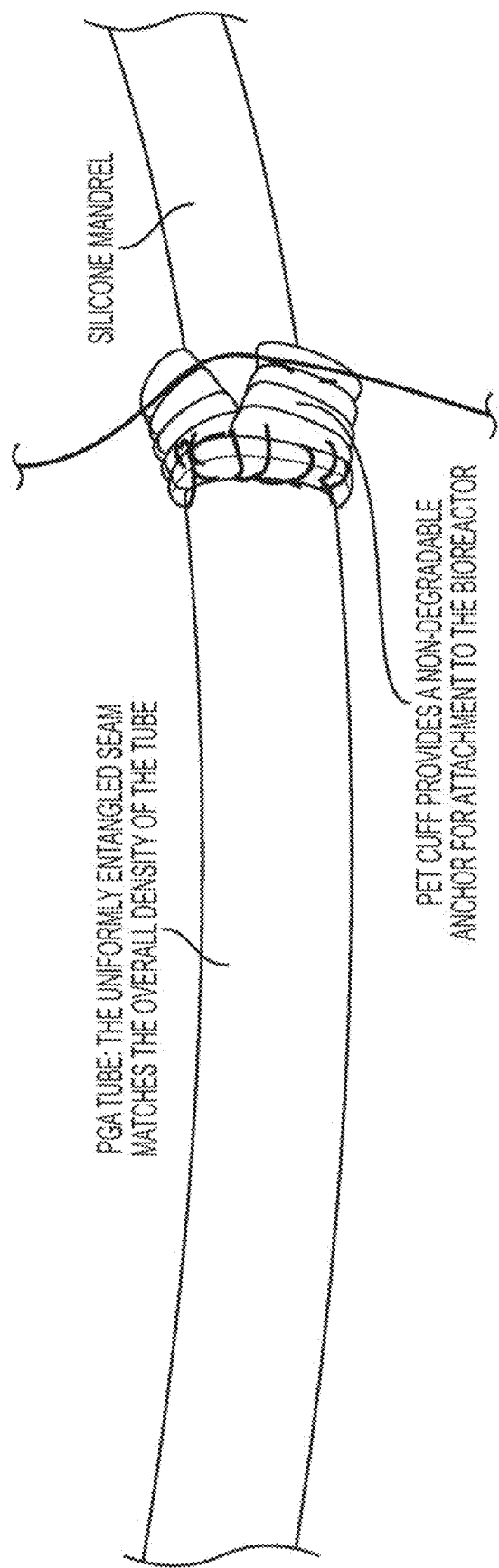
Figure 7D:
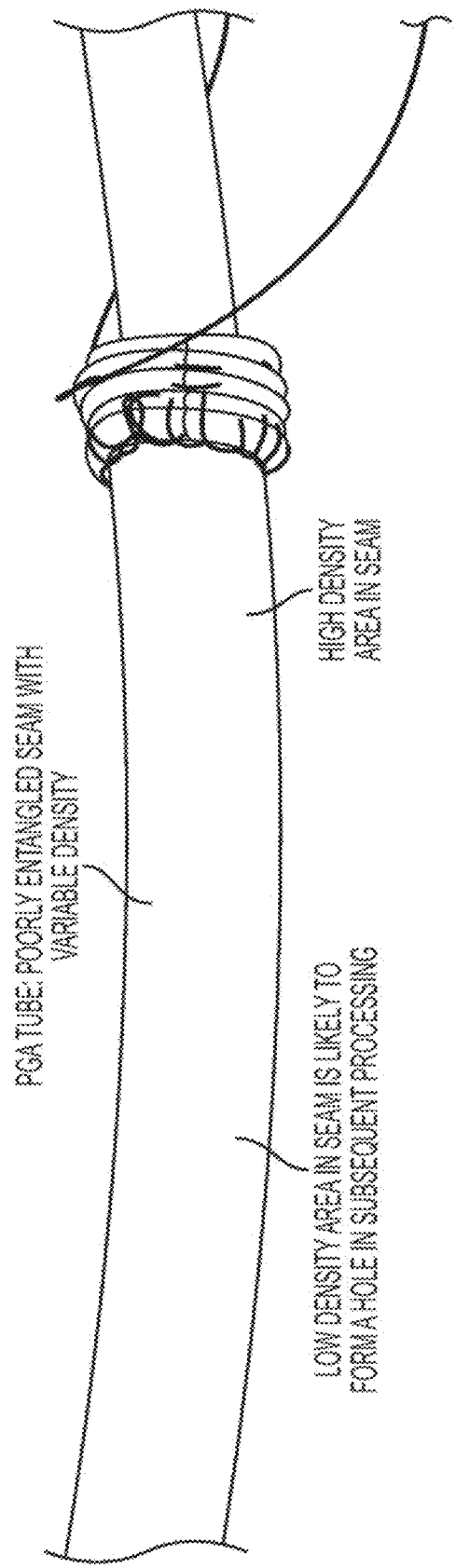

The tubular configuration of PGA shown in FIG. 7C allows cells to seed and thereafter grow in a tubular shape. A polyethylene terephthalate (PET) cuff shown in FIG. 7C supports ingrowth of tissue and thereby becomes integrated with the growing tissue. PET's non-degradable property allows it to serve as an anchor to the bioreactor to hold the tissue at a fixed length during culture. In contrast, the PGA tube degrades during the tissue growth phase. The inner diameter of the PGA tube is defined by the outer diameter of the mandrel around which the PGA scaffold is entangled, and in this case, the mandrel is made of silicone. FIG. 7C shows a silicone mandrel with outer diameter of 6 mm, and the PGA tube formed around the silicone mandrel has an inner diameter of 6 mm. As tissue forms, the contractile cells contract the polymer and tissue around the silicone tube such that the resultant tissue inner diameter is also defined by the outer diameter of the silicone tube. Inner diameter of PGA tube (and outer diameter of the silicone tube mandrel) produced readily is in the range of 3-6 mm, and tissues with smaller or larger diameters may be created by using silicone tube with the desired diameter.

A scour process is used to remove heavy metals, lubricants, and other contaminants. The PGA tube is placed on a mandrel and washed with more or more non-polar solvents and at least one primary alcohol, such as ethanol for at least 30 minutes while shaking at 25 rpm. Dry PGA tubes overnight.

Table 1 shows that this scour method substantially removes heavy metal contaminants. The presence and/or amount of heavy metal contaminants can be determined by any means know in the art; for example, by mass spectroscopy.

TABLE 1

|  | Pre-Scour, PPM | Post-Scour, PPM |
| --- | --- | --- |
| Aluminum | 15 | 2.3 |
| Barium | 0.79 | <0.05 |
| Calcium | 35 | <7 |
| Iodine | 170 | <0.07 |
| Lanthanum | 5 | <0.1 |
| Magnesium | 4.5 | <2 |
| Nickel | 3.5 | 0.31 |
| Potassium | 120 | <20 |
| Zinc | 11 | 2.7 |

Treatment of PGA with NaOH has been shown to increase the rate of PGA degradation. For example, no NaOH treatment resulted in 50% mass loss within 8.5 weeks, but 1-3 minutes of 1M NaOH treatment resulted in 65-70% mass loss within 8.5 weeks (Prabhakar et al., (2003) Engineering porcine arteries: effects of scaffold modification. *J Biomed Mat Res* 67A:303-311).

The PGA tube degrades as the tissue is cultured in the bioreactor. As the PGA degrades, cells are producing extracellular matrix proteins that form the bulk of the final graft mass. As an example, consider the following:

PGA Time 0, prior to bioreactor culture:
 PGA sheet density: 55 mg/cc
 Time 0 volume of PGA in a 6 mm-diameter graft: 0.235 cc/cm tube
 Time 0 density of PGA in a 6 mm-diameter graft is then: (55 mg/cc)*(0.235 cc/cm tube)=12.9 mg PGA/cm graft.

PGA in the final extracellular matrix protein construct, following bioreactor culture and decellularization as described below:
 PGA mass loss after 8.5 weeks in an aqueous environment at 37° C.: 30% PGA mass remains after 8.5 weeks.
 Mass PGA per cm graft: (30%)×(12.9 mg PGA/cm graft)=3.9 mg PGA/cm graft Average wet weight of a 6 mm graft: 600 mg graft/cm graft Mass PGA per mass graft: (3.9 mg PGA/cm graft)/(600 mg graft/cm)=0.0065 mg PGA/mg graft.

Therefore, PGA constitutes <1% of the final hydrated mass in this example. Similarly, using the maximum PGA density specification of 75 mg PGA/cc PGA in the same set of calculations would produce a graft with PGA as <1% of final graft mass (0.0088 mg PGA/mg graft).

Example 2

Animal Use:

All procedures were approved by their respective Animal Care and Use Committees, including Duke University, East Carolina University, and SyneCor. Animals received humane care according to the "Guide for the Care and Use of Laboratory Animals" (NIH, 1996). All surgeries and angiography were performed in sterile fashion under general anesthesia. After each surgery, graft patency was confirmed, wounds were closed, and animals were recovered. Animals were anti-coagulated with heparin (1000-5000 U) at implant. Baboons received aspirin (10 mg/kg), and dogs received dual anti-platelet therapy (325 mg aspirin/75 mg clopidogrel), daily preoperatively until the end of the study.

Formation of Extracellular Matrix Protein Constructs:

Human aortas were obtained from an American Association of Tissue Banks (AATB) accredited and FDA registered tissue bank (CryoLife, Inc.; Kennesaw, Ga.), and met criteria for implantation (FDA 21CFR1271, AATB Standards for Tissue Banking, and internal CryoLife acceptance criteria). Human smooth muscle cells (SMCs) were isolated from donor aortas (ages 17-49) that were consented for research use and tested for bioburden (aerobic bacterial and fungal contaminants), sterility, mycoplasma, and endotoxin. Cells were stored in liquid nitrogen vapor (−135° C.) prior to use. Cells from multiple donors were pooled for culture of pooled donor grafts. Human cells were used at passage 2.

Canine SMCs were isolated from canine carotid and femoral arteries, were allogeneic with respect to the construct recipient, and were used at passage 2-4.

Using an aseptic process, cells (either human or canine) were seeded onto tubular poly-glycolic acid felt scaffolds (6 mm ID for human constructs, and 3 or 4 mm ID for canine constructs) and strained cyclically (2.5% at 2.75 Hz) (Niklason, et al., Science 284, 489-493 (1999)) in a bioreactor to produce construct. Medium for growth of human constructs was high glucose DMEM with 20% serum, 5 milligram insulin per L, 5 microgram bFGF per L, 1 microgram EGF per L, 100,000 U penicillin G per L, 3 micrograms copper sulfate per L, 50 milligrams L-proline per L, 40 milligrams L-alanine per L, 50 milligrams glycine per L, and 50 milligrams ascorbic acid per L, and was changed thrice weekly. Medium for growth of canine constructs was low glucose DMEM with 20% serum, 10 ng/ml PDGF-BB, 10 ng/ml bFGF, 500 U/ml penicillin G, 3 ng/ml copper sulfate, 50 ng/ml L-proline, 20 ng/ml L-alanine, and 50 ng/ml glycine, and was changed once per week. L-ascorbic acid was added thrice weekly to canine extracellular matrix protein construct cultures.

After 7-10 weeks of culture, constructs were decellularized using aseptic processing. As described previously (Dahl, et al., Cell Transplantation 12, 659-666 (2003)), decellularization solutions comprised phosphate buffered saline (PBS) with 0.12M sodium hydroxide, 1M sodium chloride, and 25 mM EDTA, containing either 8 mM CHAPS or 0.07-1.8 mM SDS. An alternative decellularization method was also employed, in which the SDS was removed. In addition, a benzonase step may be added to digest DNA, using 2 U/mL Benzonase, 47 mM Tris, 1.4 mM magnesium chloride, and 19 mM sodium chloride, at pH 8.0. Extracellular matrix protein constructs were exposed to each solution for up to 6 hours at room temperature, and were then washed with PBS. All extracellular matrix protein constructs were decellularized prior to mechanical testing, endothelial cell seeding, and implantation. Decellularized extracellular matrix protein constructs were stored at 4° C. in phosphate buffered saline (PBS) without calcium or magnesium.

Endothelialization of Extracellular Matrix Protein Constructs:

Canine extracellular matrix protein constructs were seeded with autologous endothelial cells (ECs) in vitro prior to implantation. Canine femoral artery, carotid artery, or cephalic vein segments (3-4 cm) were cultured on fibronectin-coated plates in low glucose DMEM with 10% FBS, 1× microvascular growth supplement, 125 μg/ml heparin, and 500 U/ml penicillin G, for isolation of ECs via outgrowth from each segment. Isolation and expansion of ECs required 21±2 days, and the attachment of ECs to extracellular matrix protein constructs and shear preconditioning required an additional 2 days. For EC attachment, graft lumens were coated with fibronectin (100 μg/ml), seeded with ECs (750, 000/ml), and exposed to 11 hours of rotation at 10 rotations per hour to encourage even distribution of ECs. Shear preconditioning was performed by increasing the mean velocity of perfused culture medium in stepwise manner (10 steps total) over a 22-hour period, and maintaining the maximum mean velocity (10-15 cm/s) to match the mean velocity reported for peripheral canine arteries (10-16 cm/s (Pedley, The Fluid Mechanics of Large Blood Vessels (Cambridge University Press, Cambridge, UK, 1980)) for 13 hours prior to implant.

In vitro Analysis:

Suture retention strengths were measured by passing a loop of 6-0 Prolene® suture (BV-1 needle) through each extracellular matrix protein construct, 2 mm from the edge, and suspending weights in 10 g increments on the suture loop until the suture pulled through the tissue. Suture strength was defined as the weight in grams required to tear the tissue. Suture strengths of extracellular matrix protein constructs were measured prior to implant, and after baboon explant. Burst pressures were measured prior to implant by inflating 6 mm human extracellular matrix protein constructs, or 3-4 mm canine extracellular matrix protein constructs, with saline at room temperature until rupture, as previously described (Dahl, et al., Cell Transplantation 12, 659-666 (2003)). Burst pressure was defined as the inflation pressure at which an extracellular matrix protein construct ruptured.

For DNA quantification, extracellular matrix protein construct segments were digested with papain followed by DNA purification using a modified Qiagen silica based spin column. Resulting captured DNA was eluted using a detection compatible buffer, and DNA was quantified using a PicoGreen® assay (Life Technologies, Inc, Grand Island, N.Y., USA). Hydroxyproline was measured in papain-digested samples, using chloramine T and p-dimethylaminobenzaldehyde, and collagen was calculated as 10 times the amount of hydroxyproline Animal Models:

An old world primate model was chosen to provide phylogenetic similarity to humans, which allowed implantation of non-crosslinked human matrix-containing grafts without immunosuppression. Adult male baboons (*Papio Anubis*, 20-30 kg) are physically large enough to support implantation of a 6 mm-diameter extracellular matrix protein construct in a clinically relevant anatomic setting. Primates, however, are significantly more expensive than other animals (Rashid, et al., *Biomaterials* 25, 1627-1637 (2004)), are difficult to handle and maintain (Narayanaswamy, et al., *J Vasc Intervent Radiol* 11, 5-17 (2000)), and are limited in availability. Thus, baboons were used for arteriovenous studies, while dogs were utilized for small-diameter investigations.

The canine model (Class A Mongrel dogs, ~25 kg) was employed for the assessment of 3-4 mm diameter extracellular matrix protein constructs due to its wide acceptance in the scientific community for the evaluation of vascular prostheses (Tomizawa, et al., *Circulation* 90 (part 2), II-160-166 (1994); Bianco, et al., *Large Animal Models in Cardiac and Vascular Biomaterials Research and Testing*. B. D. Ratner, F. J. Schoen, A. S. Hoffman, J. E. Lemons, Eds., "Biomaterials Science: An Introduction to Materials in Medicine" (Elsevier Science & Technology Books, 2004)). The canine study utilized an allogeneic acellular extracellular matrix protein construct, seeded with autologous ECs, which mimics the approach proposed for eventual small-diameter clinical use Surgical Implantation Techniques:

Nine adult male baboons underwent arteriovenous placement of human extracellular matrix protein constructs (6 mm ID). One extracellular matrix protein construct was placed in the aorto-caval position for one month. Eight extracellular matrix protein constructs were placed between the axillary artery and distal brachial vein, which provided a superficial site amenable for simulating hemodialysis access, for up to six months. All anastomoses were created with a running 6-0 Prolene® suture technique.

To test long-term in vivo patency, canine extracellular matrix protein constructs (3-4 mm ID) seeded with autologous ECs were implanted end-to-side to the carotid artery in five dogs using 8-0 Prolene® suture. The intervening native carotid artery was occluded with surgical clips.

Canine extracellular matrix protein constructs (3-4 mm ID) seeded with autologous ECs were implanted into the coronary circulation of three dogs. A left thoracotomy exposed the heart. Normothermic cardiopulmonary bypass was utilized and cardiac standstill was achieved with cold cardioplegia. Each extracellular matrix protein construct was sutured to the left anterior descending coronary artery (8-0 Prolene®) and to the ascending aorta (4.0 mm aortotomy, 7-0 Prolene®), with ligation of the proximal coronary artery. After coronary bypass, animals were separated from cardiopulmonary bypass and recovered.

Immunological Assessments:

In the concordant xenogenic model of human cell-derived constructs implanted into baboon, immunogenicity of human matrix-containing constructs was assessed. Subcutaneous injections of homogenized extracellular matrix protein constructs (0.1 ml of a 0.25 mg protein/ml phosphate buffered saline, PBS) and PBS negative control (0.1 ml) were administered at days 0 and 28, with visual assessments 48-72 hours after each injection to detect whether an in vivo adaptive immune response was forming.

In addition, T-cell proliferation was measured at 0, 4, 12, and 24 weeks for baboon implants. Lymphocytes were isolated with a Ficoll gradient, and cultured 7 days in 96-well plates with segments (5 mm×5 mm) of extracellular matrix protein construct, or PTFE grafts as negative controls, in each well. Culture medium was RPMI 1640 with 10% fetal bovine serum. BrdU (100 µM) was added to each well 18 hours before cell harvest. Harvested cells were stained with 200 µL of diluted live/dead dye (Invitrogen™, Carlsbad, Calif.; L23102) for 30 min at room temperature and then with 80 µL of CD3-APC antibody (BD Pharmingin™, San Jose, Calif.; BD557597) for 50 min at room temperature, washed, permeabillized (1× Cytofix/Cytoperm™ buffer and 1× Cytoperm™ Plus; BD Biosciences, and incubated with 100 µL of DNase to partially digest DNA. Proliferating cells were stained with 50 µL of BrdU-FITC antibody (BD 559619) for 20 min at room temperature and suspended in 150 µL of 0.2% BSA/DPBS for Flow Cytometry analysis (BD Accuri™ C6). For data analysis, single cells were selected and dead cells were gated out. Proliferation rate was calculated as the percentage of CD3+/BrdU+ cells in CD3+ cells.

Duplex Ultrasound:

In the baboon model, duplex ultrasound was used to monitor midgraft extracellular matrix protein construct diameter, wall thickness, and flow rate immediately after surgery, and at 2, 4, 12, and 24 weeks.

Angiography:

Angiography was used to assess graft dilatation and narrowing. Graft patency was defined according to Fitzgibbon's classification (Fitzgibbon, et al., *J Am Coll Cardiol* 28, 616-626 (1996)).

All baboon grafts placed from the axillary artery to the brachial vein were accessed directly in mid or distal graft sections (16 G needle, 5-6 F catheters) at 1, 3, and 6-month time points (see Table 6) to determine the ability of extracellular matrix protein constructs to withstand puncture as a model for hemodialysis access.

Angiography of canine constructs was performed through a percutaneous femoral arterial approach at 1, 4, 12, 26, and 52 weeks after implant.

Computed Tomography Angiography:

Computed tomography angiography (64-slice; General Electric, Lightspeed® VCT; Fairfield, Conn., USA) of coronary bypass grafts was performed. Intravenous β-blockers minimized cardiac motion, and iohexol (350 mg I/mL) was used as contrast. Slices (0.625 mm thick) and a soft-tissue reconstruction algorithm were used for evaluation of the internal diameter and cross-sectional area of grafts.

Histology:

Tissues were fixed in 10% neutral buffered formalin, embedded in paraffin, sliced (5 µm sections), and stained with H&E, Movat's, or Alizarin Red S with a light green counterstain. Tissue sections were also prepared for cryo-sectioning by dehydrating (30% sucrose in phosphate buffered saline, PBS) and freezing in Tissue-Tek® optimal cutting temperature (OCT) compound (Sakura Finetek USA, Torrance, Calif.). Immunostaining was performed on frozen baboon sections and formalin-fixed canine sections for α-smooth muscle actin (SMC and myofibroblast marker; baboon explants: Dako M0851, 1:50 dilution (Dako, Carpinteria, Calif., USA); canine explants: Sigma A2547, 1:5000 dilution (Sigma-Aldrich; St. Louis, Mo.; USA), von Willebrand factor (protein synthesized by ECs; baboon explants: Dako M0616, 1:25 dilution; canine explants: not stained), CD3 (part of the T-cell receptor complex on mature T-lymphocytes; Abcam ab699, 1:25 dilution (Abcam, Cambridge, UK)), CD20 (protein expressed on the surface of mature B cells; Abcam ab9475, 1:25 dilution), collagen types I and III (Novus NB600-1408 and NB600-594, 1:200 dilution for both), fibronectin (Novus NB110-1635, 1:50 dilution), and vitronectin (Novus NB110-57649, 1:200 dilution) (Novus Biologicals, Cambridge, UK) with either a fluorescent or 3,3'-diaminobenzidine (DAB) stain. Alizarin-stained sections were evaluated to confirm absence of calcification (7±1 sections/animal, n=11 animals). Immunogenicity was further evaluated by observation of H&E-stained sections (11±2 sections/animal, n=12 animals) and immunostaining for CD3 and CD20 (3±1 sections/animal, n=2 animals). Neointimal thicknesses of native vessels at anastomoses were calculated as the total area of neointima divided by the length of the underlying tissue (Lumsden, et al., *J Vasc Surg* 24, 825-833 (1996)). A microscope-mounted camera and image analysis software were used for measurements.

Statistical Analysis:

Statistical analyses were performed with a Student's two-sample t-test, assuming unequal variances, for analyses with two groups. One-way ANOVA was used to determine significant differences between three or more groups, with Tukey's post-hoc comparison. Linear regression was performed to assess whether construct suture strength plotted as a function of cell donor age had a slope significantly different from 0. Two-sided P values less than 0.05 indicated statistical significance. Numeric values are presented as the mean+/−standard error of the mean. Reported 'n' represents the number of individual cultured constructs tested (not repeat segments from the same graft), and is reported in parenthesis in the tables Example 3

Generation of Extracellular Matrix Protein Constructs from Allogeneic Cells and Decellularization:

To produce extracellular matrix protein constructs (3-6 mm in diameter), allogeneic smooth muscle cells (SMCs) obtained from cadaveric donors are cultured on rapidly degradable poly-glycolic acid (PGA) tubular scaffolds in a bioreactor that delivers cyclic radial strain (Niklason, et al., *Science* 284, 489-493 (1999)). During the culture period, SMCs secrete extracellular matrix proteins, predominantly collagen, to form biosynthetic vascular tissue (Niklason, et al., *Science* 284, 489-493 (1999)), and the PGA degrades. At the end of the culture period, the resultant tissue is decellularized with detergents, leaving only the secreted collagenous matrix (Dahl, et al., *Cell Transplantation* 12, 659-666 (2003)). The decellularization process kills cells, and removes antigenic, allogeneic cells from the construct, thereby allowing the use of banked allogeneic cells to produce extracellular matrix protein constructs that are non-immunogenic and can be used in any recipient. These extracellular matrix protein constructs can be stored in a standard phosphate buffered saline (PBS) at 4° C. and immediately available for arteriovenous access creation (6 mm diameter), or for seeding with autologous ECs to reduce the risk of thrombosis associated with small diameter vascular grafting in the peripheral or coronary settings (3-4 mm graft diameters) (McAllister, et al., *Lancet* 373, 1440-1446 (2009); Kaushal, et al., *Nat Med* 7, 1035-1040 (2001); Zilla, et al., *Semin Vasc Surg* 12, 52-63 (1999)).

Example 4

Strength and Stability of Decellularized Human Extracellular Matrix Protein Constructs:

Thirty seven decellularized extracellular matrix protein constructs (6 mm diameter, 23 cm length) were produced using cells from 19 human donors, in order to assess the mechanical consistency of constructs produced from different donors (Table 2). Suture strength was measured using 6-0 Prolene® 2 mm from the edge of every construct. Burst pressure was tested intermittently on randomly selected constructs by inflating 2 cm of tubular construct with saline until rupture. Suture strengths (Table 2) did not change significantly with donor age (P=0.26; ages 17 to 49), with male versus female donor origin (P=0.52), or with use of single donor versus pooled donor populations (2-6 donors per pool) for graft culture (P=0.42). A group of extracellular matrix protein constructs were randomly selected and stored for 12 months. Extracellular matrix protein constructs retained their strength, without significant changes in suture strength, burst pressure, or compliance (P=0.97, P=0.18, and P=0.48, respectively) after 12 months of storage at 4° C. in phosphate buffered saline (PBS), and were within the ranges reported for native human vasculature (Table 3). Extracellular matrix protein constructs contained residual PGA fragments (1.1±0.1% of cross-sectional area of extracellular matrix protein constructs histological sections prior to storage), which did not degrade further during storage at 4° C. (1.0±0.1% after 9 months of storage, P=0.54).

Table 2 shows donor data and suture strengths for 6 mm-diameter decellularized human extracellular matrix protein constructs. All data are presented as Mean±SEM (number of distinct grafts tested).

TABLE 2

| Human Donor | Donor Age | Donor Sex | Diabetic | Smoker | Hypertension | Other Diseases | g Suture Strength |
|---|---|---|---|---|---|---|---|
| 1 | 17 | F | No | No | No | Mitral Valve Prolapse; Asthma | 250 (1) |
| 2 | 19 | M | No | No | No | None | 233 ± 20 (4) |
| 3 | 25 | F | No | No | No | None | 130 ± 20 (2) |
| 4 | 33 | F | No | No | No | None | 80 (1) |
| 5 | 34 | F | No | Yes | No | None | 223 ± 27 (4) |
| 6 | 45 | F | No | Yes | Yes | Asthma | 120 ± 10 (2) |
| 7 | 46 | M | No | Yes | Yes | None | 110 (1) |
| 8 | 46 | M | Yes | Yes | No | None | 115 ± 5 (2) |
| 9 | 46 | M | Yes | Yes | Yes | Kidney Failure | 135 ± 35 (2) |
| 10 | 47 | M | No | No | No | Gastroesophageal Reflux Disease | 275 ± 42 (4) |
| 11 | 47 | M | No | Yes | No | None | 120 ± 30 (2) |
| Pool of Donors 9 and 12 | 46 43 | M M | Yes No | Yes Yes | Yes Yes | Kidney Failure None | 155 ± 35 (2) |

TABLE 2-continued

| Human Donor | Donor Age | Donor Sex | Diabetic | Smoker | Hypertension | Other Diseases | g Suture Strength |
|---|---|---|---|---|---|---|---|
| Pool of Donors 1, 4, 5, 7, 8 and 10 | 17 | F | No | No | No | Mitral Valve Prolapse; Asthma | 140 (1) |
| | 33 | F | No | No | No | None | |
| | 34 | F | No | Yes | No | None | |
| | 46 | M | No | Yes | Yes | None | |
| | 46 | M | Yes | Yes | No | None | |
| | 47 | M | No | No | No | Gastroesophageal Reflux Disease | |
| Pool of Donors 13, 14, and 15 | 18 | M | No | No | No | None | 146 ± 5 (7) |
| | 27 | F | No | No | No | None | |
| | 43 | M | No | No | Yes | Herpes | |
| Pool of Donors 16, 17, 18, and 19 | 17 | F | No | No | No | None | 265 ± 25 (2) |
| | 27 | M | No | Yes | No | None | |
| | 47 | M | No | Yes | Yes | Arthritis | |
| | 49 | F | No | Yes | No | None | |

Table 3 shows mechanical properties of extracellular matrix protein constructs before and after 12 months of storage, and native comparators.

TABLE 3

| | g Suture Strength | mmHg Burst Pressure | % Compliance per 100 mmHg |
|---|---|---|---|
| 6 mm diameter human constructs | 178 ± 11 (37) | 3337 ± 343 (10) | 3.3 ± 0.8 (10) |
| 6 mm diameter human constructs stored 12 months | 170 ± 22 (9) | 2651 ± 329 (5) | 2.5 ± 0.8 (5) |
| Human saphenous vein | 196 ± 29 (7) | 1599 ± 877 (7) | 0.7-1.5 |
| Human internal mammary artery | 138 ± 50 (6) | 3196 ± 1264 (16) | 11.5 ± 3.9 (7) |

Table 4 shows the minimum and maximum wall thickness and Table 5 shows the beta-actin, lipid and hydroxyproline content of the decellularized extracellular matrix protein constructs of the present invention as compared to cellular based constructs or fresh native tissue.

TABLE 4

| Min Wall Thickness (um) | Max Wall Thickness (um) | Beta Actin (ng/cm graft length) | Lipid (% dry weight) | Hydroxyproline (mg/g dry weight) |
|---|---|---|---|---|
| 391 ± 22 (23) | 586 ± 33 (23) | 41 ± 4 (22) | 1.1 ± 0.1 (23) | 60 ± 2 (14) |

Previous reports on engineered tissues made from human cells have yielded significantly lower suture strengths (59 g), significantly lower burst pressures (59-108 mmHg), significantly lower average wall thicknesses (181 micrometers), and significantly lower hydroxyproline content (5-16 mg/g dry weight) (Poh, et al., Lancet 365, 2122-2124 (2005); McKee, et al., EMBO Rep 4, 633-638 (2003)). This superiority of the current constructs as compared to those of Poh et al may be due to the use of lower-passage human cells, as well as the specific medium composition that was utilized during bioreactor culture, both of which may have contributed to superior cell growth, collagenous matrix production, and hence improved mechanical properties.

TABLE 5

| | Beta Actin (ng/cm graft length) | Lipid (% dry weight) |
|---|---|---|
| Fresh | 1958 ± 479 (7) | 1.9 ± 0.2 (6) |
| Decell | 41 ± 4 (22) | 1.1 ± 0.1 (23) |

The constructs of the present invention are devoid of living cells. Beta actin and Lipid contents are reduced via decellularization. In contrast, a devitalization approach that kills cells, but does not remove the cellular remnants, likely retains concentrations of beta actin and lipid that resemble concentrations of a fresh tissue.

Example 5

Figure 2A:
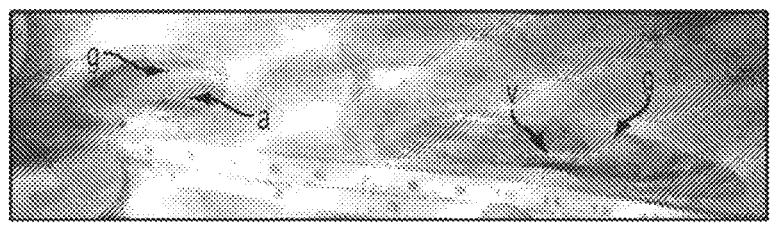
FIGS. 2A-2G are photographs showing implant sites and observations.
Figure 2B:
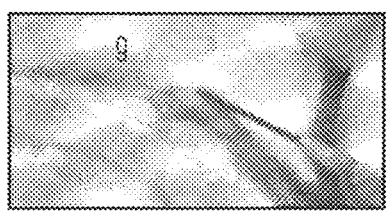
Figure 2C:
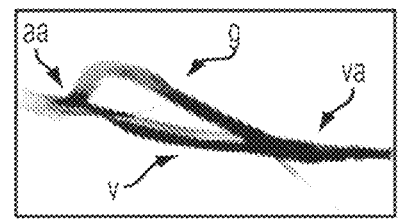

Decellularized Human Extracellular Matrix Protein Constructs in an Arteriovenous Model:

To assess the function of 6 mm extracellular matrix protein constructs, nine extracellular matrix protein constructs grown from human cells (6 mm diameter, 12.5±1.1 cm length) were implanted into baboons as arteriovenous conduits (FIG. 2A) and were observed for 1-6 months (Table 6). One animal was excluded after pulling open the surgical incision site, exposing the construct and creating a wound infection. No infection was observed in the 8 remaining animals. Duplex ultrasound measurements of extracellular matrix protein constructs at weeks 0, 2, 4, 12, and 24 (Table 7) showed no change in diameter (P=0.28), no change in wall thickness (P=0.93), and an increase in flow rate between weeks 0 and 2 (P<0.01). Flow through extracellular matrix protein constructs (Table 7) was sufficient for hemodialysis (>300 mL/min (B. Dixon, *Kidney Int* 70, 1413-1422 (2006)). Extracellular matrix protein constructs were accessed initially at 4 weeks (FIG. 2B), which is a clinically relevant time for first access to allow for integration and remodeling of hemodialysis grafts, and then at 3 and 6 months. Of the eight arteriovenous extracellular matrix protein constructs, 2/2 were patent at 1-month, 2/3 were patent at 3-month explant, and 3/3 were patent at 6-month explant (FIG. 2C). Only one construct showed thrombosis at 3 months, likely due to technical difficulties with access, which required prolonged manual pressure that led to clotting. Hence, the patency of the arteriovenous 6 mm extracellular matrix protein constructs in the baboon was 88% (⅞). No aneurysmal dilatation and no calcification were observed in any construct. Furthermore, constructs did not exhibit substantial intimal hyperplasia. Anastomotic neointimal hyperplasia at 6 months (luminal hyperplasia thickness of 0.11±0.05 mm) was less than that reported at 1 month for PTFE arterial bypass grafts in a baboon model (0.25±0.09 mm) (Lumsden, et al., *J Vasc Surg* 24, 825-833 (1996)).

Figure 8A:
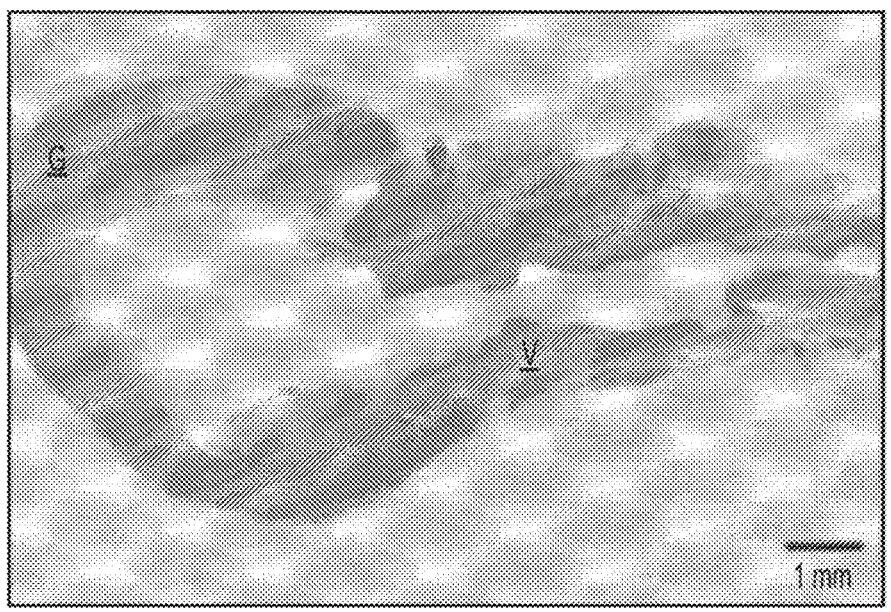
FIGS. 8A-B are photographs of venous intimal hyperplasia.
Figure 8B:
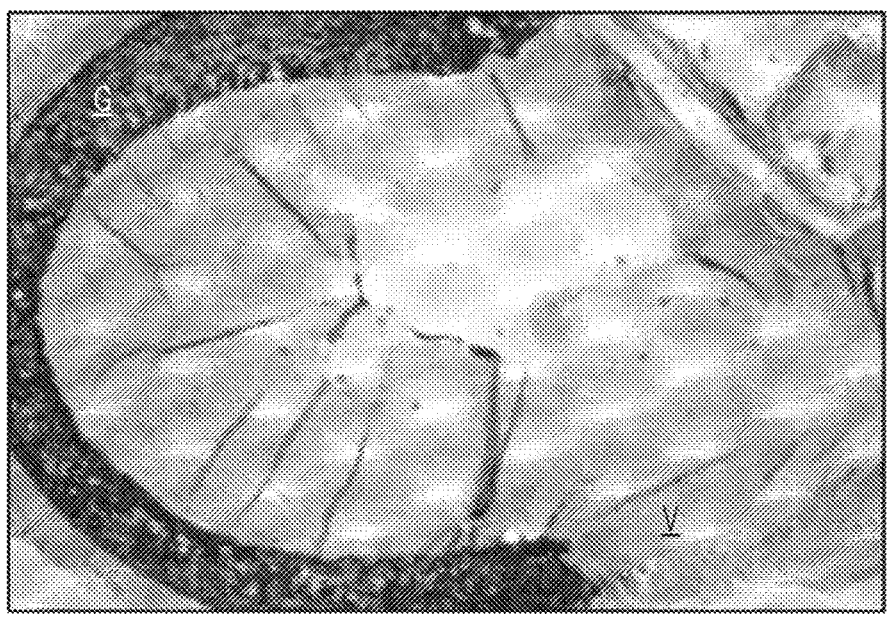
Figure 9A:
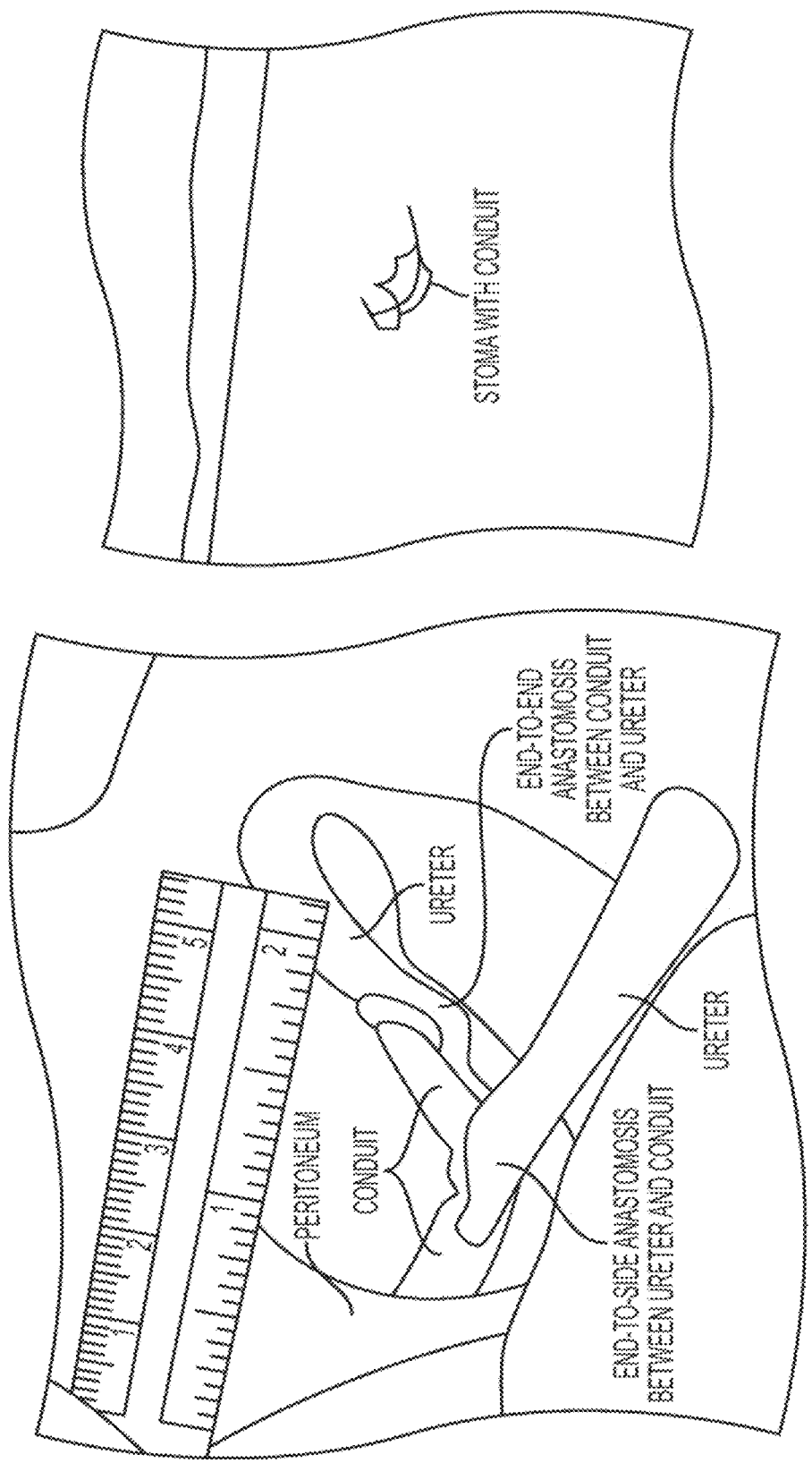
FIGS. 9A-E is a series of photographs and diagrams showing usage of the extracellular matrix protein constructs of the present invention as urinary conduits.
Figure 9B:
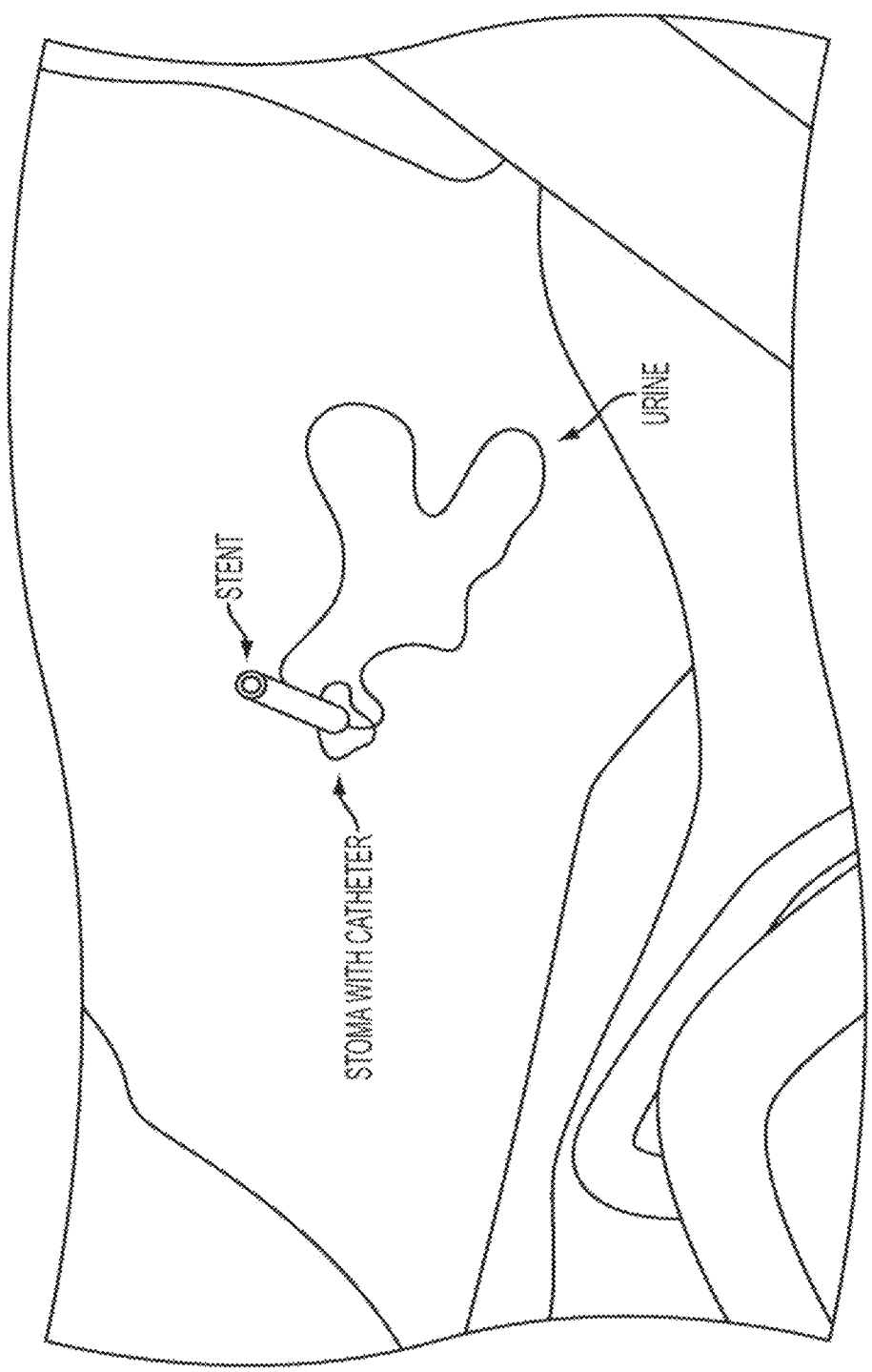
Figure 9C:
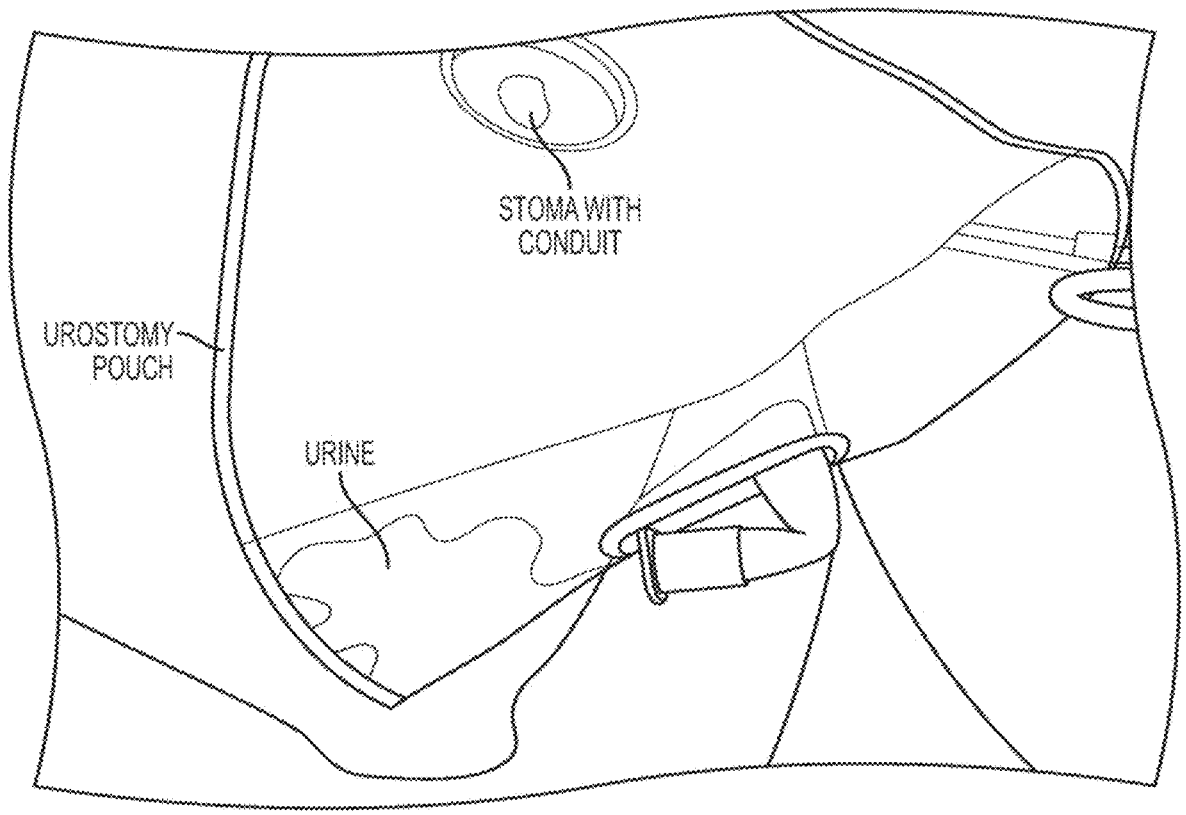
Figure 9D:
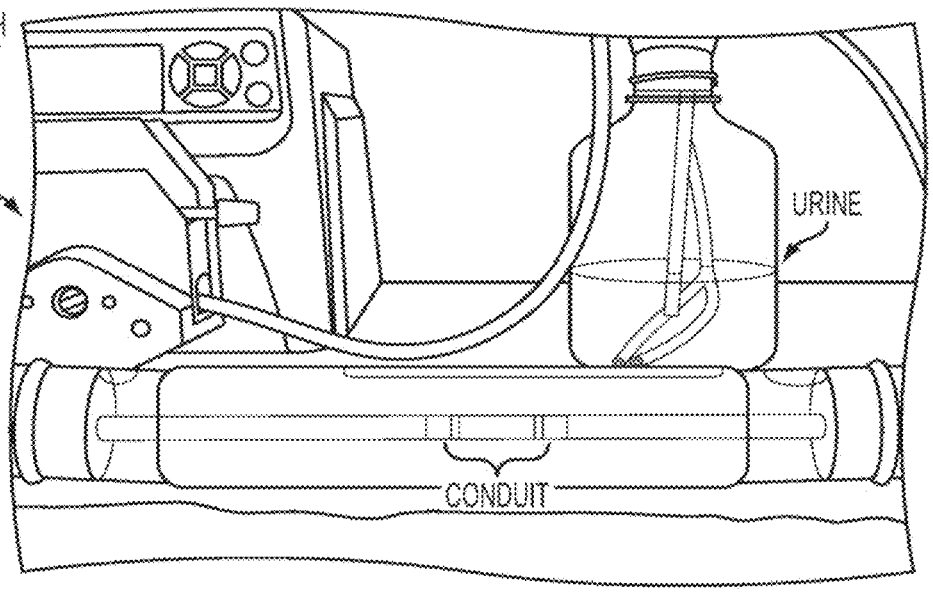
Figure 9E:
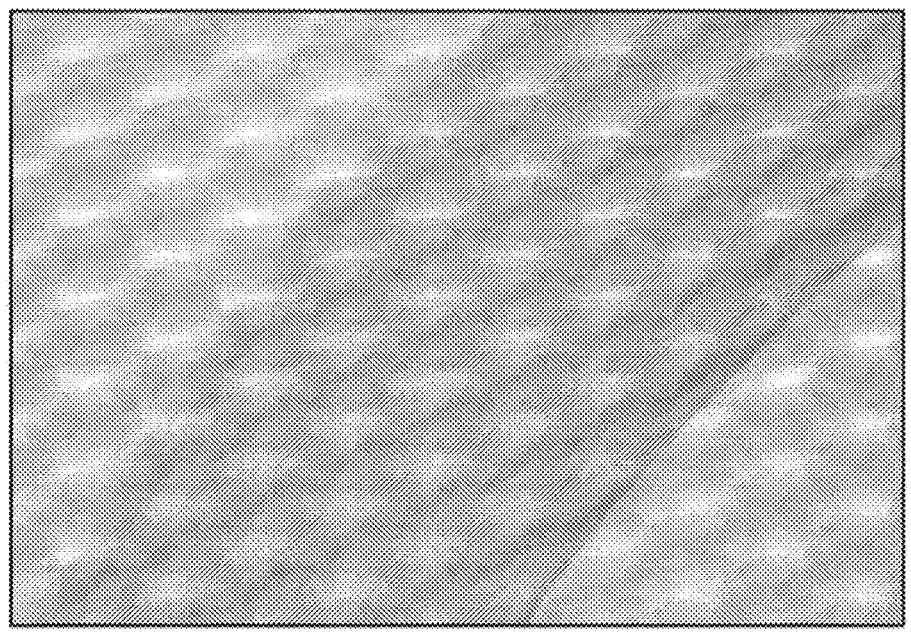
Figure 9E:
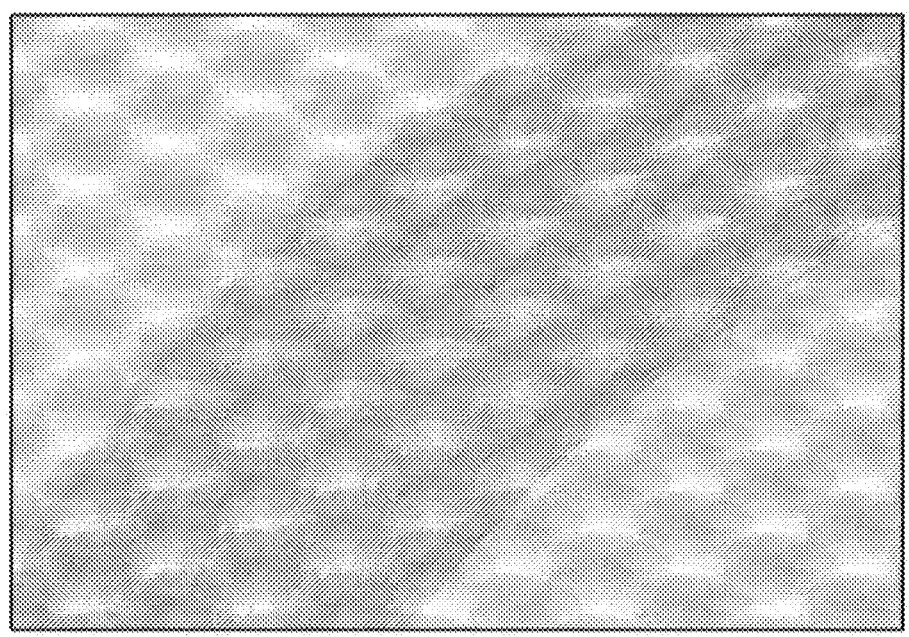

Venous intimal hyperplasia is minimal at 3 months for extracellular matrix protein constructs in a baboon model. The venous anastomosis of an extracellular matrix protein construct is shown in FIG. 8A, with the construct (G) on the left and the vein (V) on the right. Only small patches of intimal hyperplasia are visible on the vein, and these patches are circled. In contrast, FIG. 8B shows that the vein adjacent to a PTFE graft has substantially more intimal hyperplasia (see circled region as an example of the thickness of intimal hyperplasia) in a human. Further, the extent of intimal hyperplasia in the graft section is also minimal for the extracellular matrix protein construct and substantial for the PTFE graft (Prichard et al., An early study on the mechanisms that allow tissue-engineered vascular grafts to resist intimal hyperplasia. J Cardiovasc Transl Res 4 (5):674-682, 2011).

Table 6 shows a summary of implanted extracellular matrix protein constructs.

TABLE 6

|  | Graft Inner Diameter (mm) | Autologous EC's Seeded | Graft Access Time Points (Months) | Aneurysmal Dilatation | Patent |
|---|---|---|---|---|---|
| Human Constructs in a Baboon Arteriovenous Model |  |  |  |  |  |
| 1 Month | 6 | No | No Access | No | Yes |
| 1 Month | 6 | No | 1 | No | Yes |
| 3 Months | 6 | No | 1 | No | No |
| 3 Months | 6 | No | 1, 3 | No | Yes |
| 3 Months | 6 | No | 1, 3 | No | Yes |
| 6 Months | 6 | No | 1, 3, 6 | No | Yes |
| 6 Months | 6 | No | 1, 3, 6 | No | Yes |
| 6 Months | 6 | No | 1, 3, 6 | No | Yes |
| Excluded | 6 | No | Excluded | Excluded | Excluded |
| Canine Constructs in a Canine Carotid Artery Bypass Model |  |  |  |  |  |
| 1 Week | 3 | Yes | NA | No | No |
| 1 Month | 3 | Yes | NA | No | Yes |
| 12 Months | 3 | Yes | NA | No | Yes |
| 12 Months | 4 | Yes | NA | No | Yes |
| Excluded | 3 | Yes | Excluded | Excluded | Excluded |
| Canine Constructs in a Canine Coronary Artery Bypass Model |  |  |  |  |  |
| 1 Week | 3 | Yes | NA | No | Yes |
| 1 Month | 3 | Yes | NA | No | Yes |
| Excluded | 3 | Yes | Excluded | Excluded | Excluded |

Table 7 shows duplex ultrasound measurements of extracellular matrix protein constructs placed as arteriovenous grafts in baboons.

TABLE 7

|  | Week 0 | Week 2 | Week 4 | Week 12 | Week 24 |
|---|---|---|---|---|---|
| Diameter (mm) | 5.8 ± 0.2 (7) | 6.3 ± 0.3 (7) | 6.7 ± 0.3 (7) | 6.8 ± 0.6 (5) | 6.3 ± 0.2 (3) |
| Wall thickness (mm) | 1.0 ± 0.1 (7) | 0.9 ± 0.1 (7) | 1.0 ± 0.1 (7) | 1.1 ± 0.2 (5) | 1.0 ± 0.1 (3) |
| Flow rate (ml/min) | 764 ± 216 (7) | 2278 ± 430 (7) | 1464 ± 124 (7) | 1559 ± 379 (5) | 1572 ± 301 (3) |

Example 6

Extracellular Matrix Protein Constructs in Small Diameter Peripheral and Coronary Arterial Bypass Models:

The function of small diameter (3-4 mm) extracellular matrix protein constructs was evaluated in canine models of peripheral and coronary artery bypass. Canine extracellular matrix protein constructs were produced from allogeneic canine cells, decellularized, and luminally seeded with autologous ECs from the intended recipient. Attached ECs were elongated and aligned within the lumens of extracellular matrix protein constructs, but complete EC coverage was never achieved. Rather, EC coverage varied widely between constructs, with a coverage range of 0-60% (14±8%) on sections sampled from constructs prior to implant. In general, canine constructs were less strong than human constructs, although still suitable for implantation (burst pressures were 1618±67 mmHg for 3 mm canine grafts; n=39).

Figure 2D:
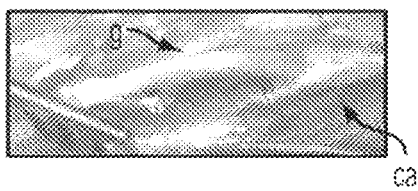
Figure 2E:
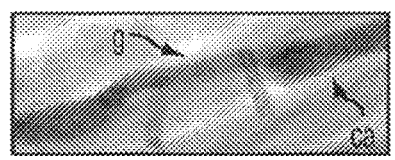

Five endothelialized canine extracellular matrix protein constructs (3-5 cm in length) were implanted as carotid artery bypass grafts, with follow-up times of 1 week to 12 months (FIG. 2D). One animal was excluded after dying acutely with a patent graft. One graft occluded at 1 week. All other constructs remained patent, including two constructs that were followed for one year (Table 6). A representative angiogram at one year (FIG. 2E) demonstrated excellent long-term patency. No stenosis or dilatation was observed in implanted constructs, and no intimal hyperplasia was observed at anastomoses.

Figure 2F:
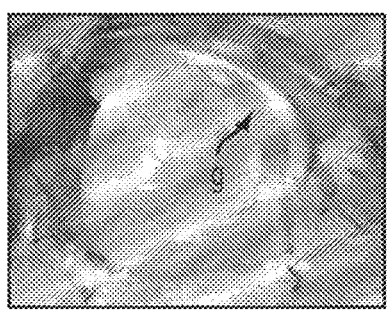
Figure 2G:
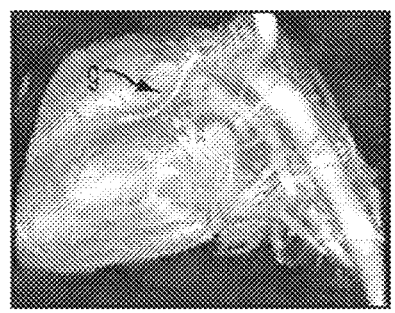

Three endothelialized canine extracellular matrix protein constructs (7-10 cm in length) were also implanted into the left anterior descending coronary artery of dogs (FIG. 2F) and followed for up to 1 month (Table 6). One animal died the day after implantation with a patent construct and was excluded from the study. All coronary artery bypass constructs were patent at 1 week and 1 month explants (FIG. 2G). For all small-diameter canine extracellular matrix protein constructs (a total of 6 in the carotid and coronary circulations), primary patency was 83% (⅚)

Example 7

Figure 3A:
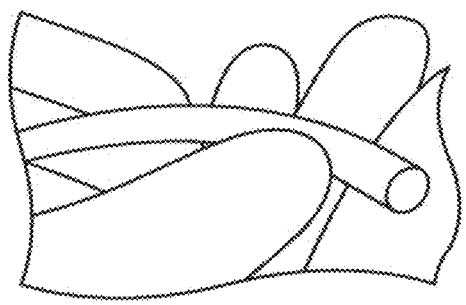
FIGS. 3A-3F is a diagram and photographs showing decellularized human constructs, pre-implant.
Figure 3B:
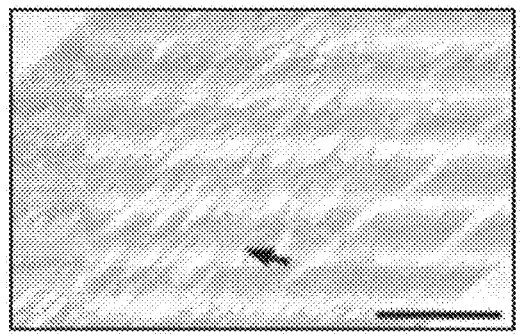
Figure 3C:
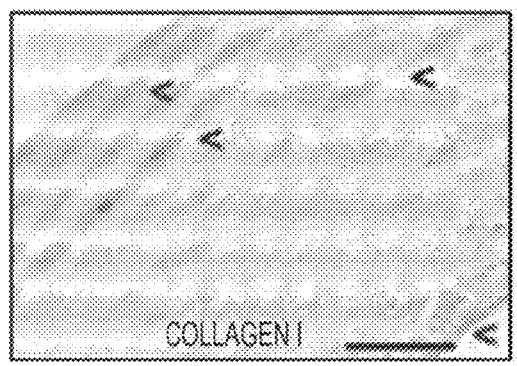
Figure 3D:
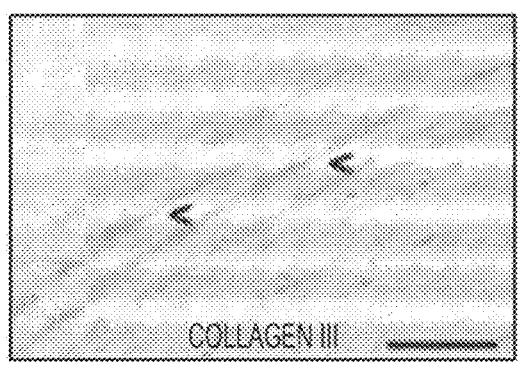
Figure 3E:
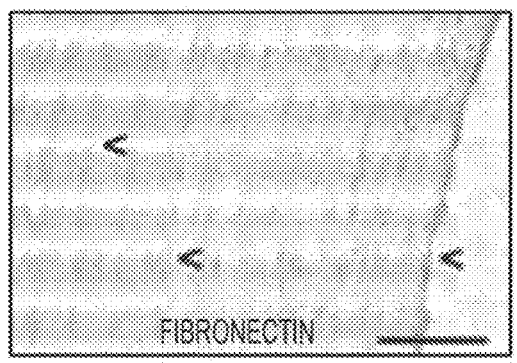
Figure 3F:
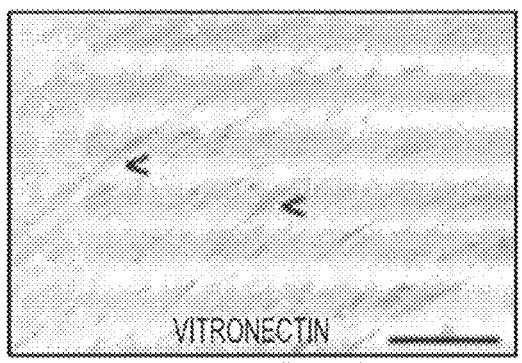

Remodeling of Extracellular Matrix Protein Constructs In Vivo:

Prior to implant, extracellular matrix protein constructs were smooth and uniform (FIG. 3A). Histological evaluation (FIG. 3B), as well as DNA quantification (0.74±0.10 µg DNA/mg dry tissue weight), demonstrated that the extent of decellularization of extracellular matrix protein constructs was similar to that of other decellularized scaffolds used clinically (Derwin, et al., *J Bone Joint Surg Am* 88, 2665-2672 (2006)). The extracellular matrix of the constructs contained collagen types I and III, which are the most prevalent types in native vasculature, as well as fibronectin and vitronectin, all with primarily circumferential alignment (FIG. 3).

Figure 4A:
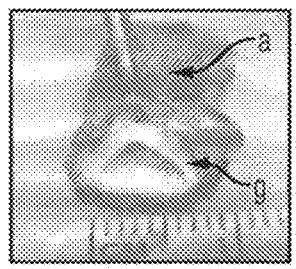
FIGS. 4A-4I are photographs showing explanted constructs remodeled in vivo.
Figure 4B:
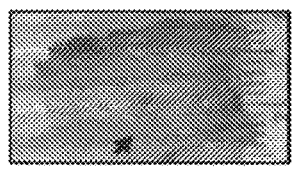

After implantation into baboons and canines, extracellular matrix protein constructs showed considerable remodeling. For all grafts, gross analysis at explant revealed a smooth inner graft tissue surface with formation of a loose fibrous outer "adventitial" tissue layer (FIG. 4A). Extracellular matrix protein constructs demonstrated a notable lack of constrictive fibrotic tissue surrounding grafts at explant (FIG. 4A). Constructs integrated well with the native vasculature at anastomotic sites (FIG. 4B).

Figure 4C:
Figure 4D:
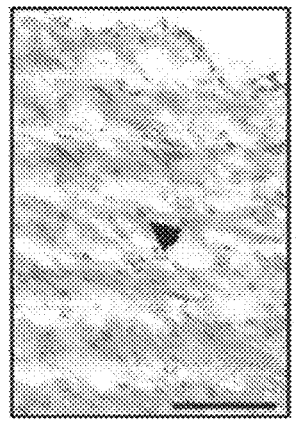
Figure 4E:
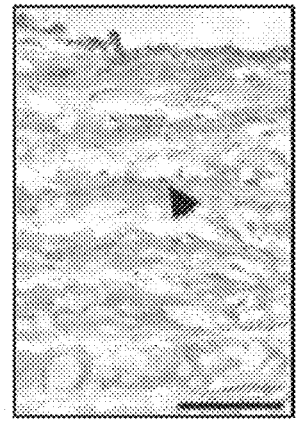
Figure 4F:
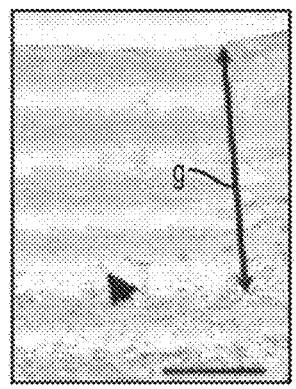

Extracellular matrix protein constructs remodeled to become compositionally more similar to native artery after implantation. Within 3 months after implant, elastin formed in anastomotic sections of grafts explanted from baboons (FIG. 4C) in regions containing the highest density of infiltrated host cells (FIG. 4D). No elastin was observed midgraft in any explanted extracellular matrix protein constructs. Alpha-smooth muscle actin positive cells, which could be either SMCs or myofibroblasts, densely populated the full thickness of extracellular matrix protein constructs near anastomotic sites (FIG. 4E), suggesting migration from adjacent native vasculature. Actin-positive cells appeared to infiltrate transmurally from the adventitial-like tissue layer into extracellular matrix protein constructs in midgraft regions, starting at 6 months in the baboon model (FIG. 4F).

Figure 4G:
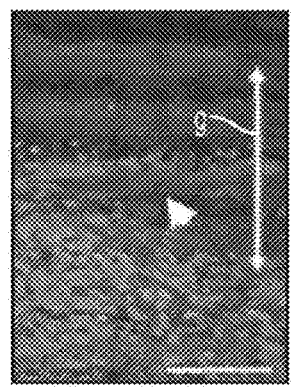
Figure 4H:
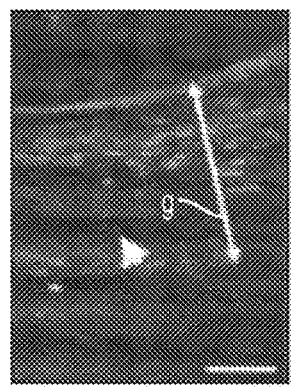
Figure 4I:
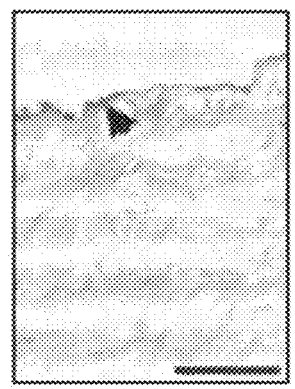

In the canine model, α-smooth muscle actin positive cells began to infiltrate midgraft sections transmurally by 1 month (FIG. 4G) and were observed throughout the midgraft wall by 1 year (FIG. 4H). Host cell infiltration into midgraft extracellular matrix protein construct walls was more rapid in the canine model, possibly because shorter grafts were placed in the canines or because of differences in species. In both models, there were fewer cells within the extracellular matrix protein construct walls in midgraft sections (FIG. 4F, Fig. G, Fig. H) than sections near the anastomoses (FIG. 4D, Fig. E). Von Willebrand factor (an EC marker) positive cells were observed on luminal surfaces of extracellular matrix protein constructs both near anastomotic sites and midgraft in both canine grafts (which were endothelialized prior to implantation) and baboon grafts (which were not) (FIG. 4I). ECs may have migrated from anastomosed vascular tissue, migrated transmurally from surrounding tissue (Zilla et al., *Biomaterials* 28, 5009-5027 (2007)), or originated from circulating progenitor cells (Asahara, et al., *Science* 275, 964-967 (1997)).

In the baboon study, midgraft extracellular matrix protein construct segments were saved for mechanical testing and collagen analysis at explant. Explanted extracellular matrix protein constructs displayed increased suture strength (276±28 g, n=8, P=0.01), but no significant changes in burst pressure (3646±582 mmHg, n=4, P=0.67) or compliance (3.4±2.3% per 100 mmHg, n=4, P=0.70) compared to the pre-implant values reported in Table 3. Thus, extracellular matrix protein constructs were mechanically robust without complete infiltration of cells into midgraft sections (FIG. 4F) or elastin in midgraft sections. No significant changes in collagen density were observed between extracellular matrix protein constructs pre-implant (57±5%, n=8), extracellular matrix protein constructs at explant (46±5%, n=7), inflow axillary artery (46±5%, n=7), or control axillary artery explanted from the non-implant arm (42±3%, n=7; P=0.07).

Figure 5A:
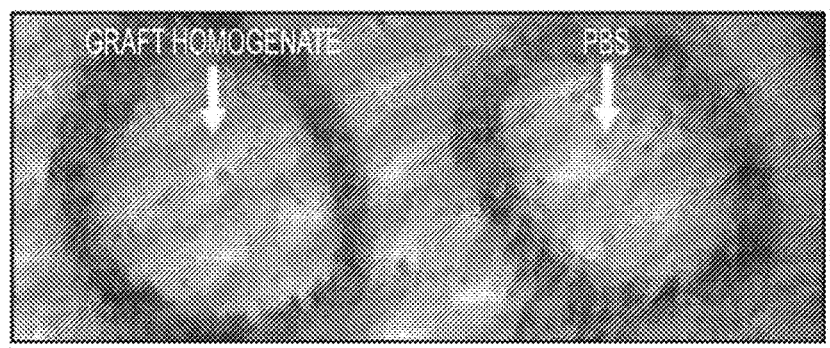
FIGS. 5A-5F are photographs and a graph showing that the extracellular matrix protein constructs were not immunogenic.
Figure 5B:
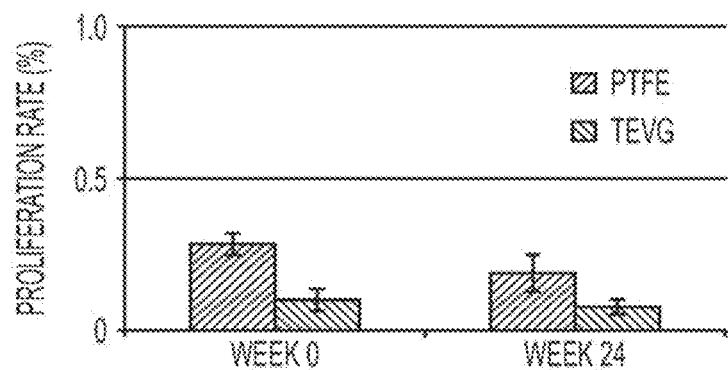
Figure 5C:
Figure 5D:
Figure 5E:
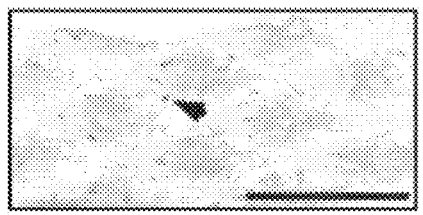
Figure 5F:
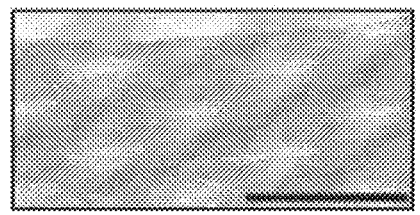

Extracellular matrix protein constructs were not immunogenic. Injections of homogenized extracellular matrix protein construct, and PBS as a negative control, were placed intradermally in every baboon at the time of graft implant and again 4 weeks post implantation (FIG. 5A). The absence of visible induration or redness at all injection sites indicated that recipients were not sensitized to graft material. Immunogenicity of grafts was also assessed by sampling blood from baboons with implanted extracellular matrix protein constructs, and measuring in vitro proliferation of T-cells exposed to PTFE grafts (negative control) or extracellular matrix protein constructs (FIG. 5B). Immunostaining of dense cellular regions (FIG. 5C) showed only sparse populations of CD3 or CD20 positive cells (FIG. 5D, Fig. E), which were often undetectable in midgraft sections. Foreign body giant cells were not observed in any explanted extracellular matrix protein construct. Finally, calcification, which is commonly observed in xenogenic or elastin-containing vascular grafts (Hilbert, et al., *J Biomed Mater Res A* 69, 197-204 (2004); Hopkins, et al., *J Thorac Cardiovasc Surg* 137, 907-913, 913e901-904 (2009)), was not observed in any extracellular matrix protein construct in any model (FIG. 5F).

Example 8

Extracellular matrix protein constructs were generated by culturing human cadaveric donor cells or canine cells on a degradable PGA scaffold to support synthesis of a collagenous extracellular matrix. Antigenic cellular material was removed via a detergent-based decellularization step to render tissues non-immunogenic. The extracellular matrix protein constructs contained minimal PGA fragments and retained mechanical properties similar to native vessels after 12 months of storage in buffer at 4° C. Function of 6 mm diameter human extracellular matrix protein constructs was demonstrated in a baboon arteriovenous model. Small diameter (3-4 mm) canine extracellular matrix protein constructs were luminally seeded with ECs, and implanted in canine models of peripheral and coronary bypass. Extracellular matrix protein constructs integrated well with native vasculature at anastomotic sites and resisted intimal hyperplasia. Infiltration of α-smooth muscle actin positive cells, ECs on graft lumens, and elastin formation near anastomoses was observed. Long-term patency was demonstrated for up to one year.

Figure 6:
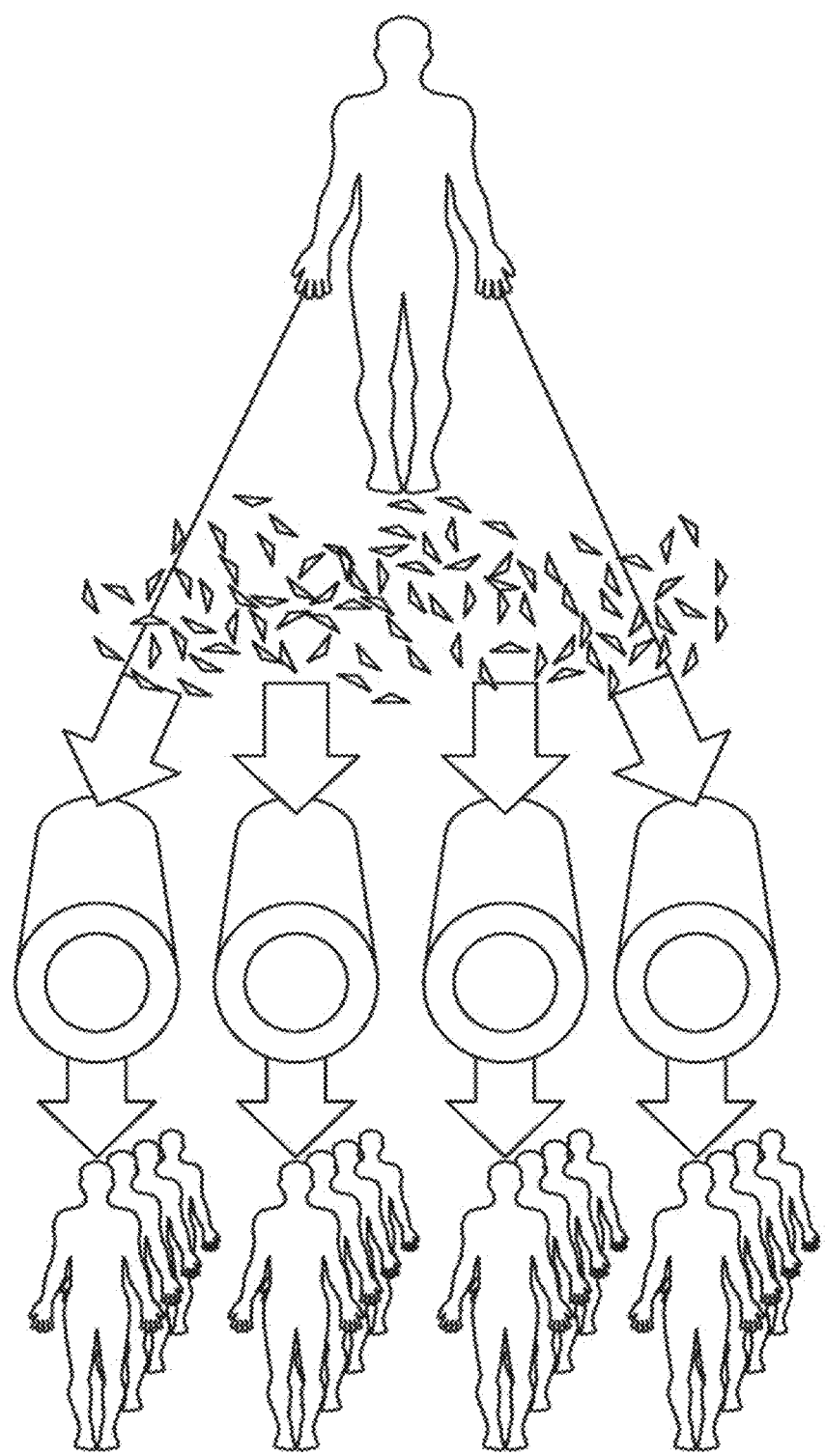
FIG. 6 is a schematic illustration in which one donor's cells are used to produce many extracellular matrix protein constructs for many recipients.

One approach of using allogeneic human cells to produce extracellular matrix protein constructs allows one human donor to provide grafts for dozens of patients (FIG. 6). This approach differs significantly from the one-donor-to-one-recipient model, which pertains to autologous tissue engineering and to cadaveric human or animal blood vessels. One human donor provides a cell bank large enough to produce 37 large diameter (6 mm internal diameter) extracellular matrix protein constructs or 74 small diameter (3 mm ID) extracellular matrix protein constructs. Pooling cells from multiple donors allows for the generation of large cell banks, which in turn makes possible the manufacture of many extracellular matrix protein constructs per cell bank (i.e., 200-500 units). This offers greater economies of scale than completely autologous tissue engineering approaches. Further, use of allogeneic cells, combined with decellularization and simple storage methods, allows the culture period for graft production to be moved "off-line." Therefore, patients have no waiting period for graft production since the grafts have already been created and stored. The ability to store grafts is an important step in making extracellular matrix protein constructs available to the patient immediately at their time of need, as opposed to custom made grafts for each patient. This is an important departure from cell-containing products, which generally cannot be stored long term without specialized cryopreservation equipment and laborious thawing procedures (Pascual, et al., *Ann Vasc Surg* 15, 619-627 (2001)).

Example 9

A porcine model was used to evaluate the conduit for urinary diversion. Both ureters were anastomosed to the conduit in Wallace fashion. A urinary diversion stent was placed in each ureter to prevent both early anastomotic leakage and stricture, during the normal postoperative phase of ureter swelling. A plug of skin and subcutaneous tissue was removed in order to accommodate the conduit. A cruciate incision was created in the fascia, the muscle was split, and a cruciate incision was created in the posterior rectus sheath. Then, the conduit was brought through the abdominal wall, and secured to the skin and subcutaneous tissue with suture. A skin barrier and ostomy pouch was adhered to the skin surrounding the stoma for urine collection. Tunneling in the retroperitoneal plane keeps the graft out of the abdominal cavity, which minimizes risk of forming adhesions between the graft and other abdominal tissues. This is important because adhesion formation is a real clinical problem. Tunneling the graft in the retroperitoneal plane, the anastomoses with the ureters, and the anastomosis at with the skin at the stoma site, all provide exposure to a source of vascularization, which may aid in resistance of infection. Exposure to the peritoneum, skin, ureters, and urine also may provide a source of cells to populate the conduit. FIGS. 9A-9E show the usage of the extracellular matrix protein constructs of the present invention as urinary conduits. The results show that the conduits tolerate chronic exposure to urine. Concentrated human urine was collected, and pumped through a segment of the urinary conduit graft for 4 weeks at 37° C. After 4 weeks of urine circulation, the graft resisted active diffusion of urine through the graft wall. This lack of significant diffusion across the wall of the conduit is demonstrated by the observation that concentrated urine in the bottle was darker than the liquid external to the graft in the flow loop (this liquid was phosphate buffered saline, PBS). In contrast, ileal conduits, which are the current gold standard graft material for urinary diversions, actively absorb their contents.

Table 8 shows suture strength of the urinary conduit before and after 4 weeks of urine exposure.

TABLE 8

| | Suture Pullout Strength (g) |
|---|---|
| Graft prior to urine exposure | 280 ± 35 |
| Graft in urine for 4 weeks | 275 ± 15 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A tubular scaffold comprising tubular biodegradable non-woven polyglycolic acid wherein the density of the polyglycolic acid is 45 mg/cc to 75 mg/cc and said density is uniform across the entire tubular scaffold, wherein the thickness of the polyglycolic acid is 0.8 to 1.2 mm and wherein the scaffold comprises polyglycolic acid fibers and the thickness of the fibers within the polyglycolic acid is 5 to 20 μm, and wherein the scaffold is substantially free of heavy metal contaminants, wherein the tubular scaffold is an ex vivo cell culture tubular scaffold.

2. The scaffold of claim 1, wherein the length of the scaffold is 1 cm to 100 cm.

3. The scaffold of claim 1, wherein the length of the scaffold is 10 cm to 40 cm.

4. The scaffold of claim 1, wherein the inner diameter of the scaffold is 3 mm to 6 mm.

5. The scaffold of claim 1, wherein the scaffold comprises trace amounts of heavy metal contaminants selected from the group consisting of: aluminum, barium, calcium, iodine, lanthanum, magnesium, nickel, potassium and zinc.

6. The scaffold of claim 1, wherein the scaffold comprises non-biodegradable supports at each end.

7. A composition comprising
(a) a tubular scaffold comprising biodegradable nonwoven polyglycolic acid, wherein the density of the polyglycolic acid is 45 mg/cc to 75 mg/cc and said density is uniform across the entire tubular scaffold, wherein the thickness of the polyglycolic acid is 0.8 to 1.2 mm and wherein the scaffold comprises polyglycolic acid fibers and the thickness of the fibers within the polyglycolic acid is 5 to 20 μm, wherein the tubular scaffold is an ex vivo cell culture tubular scaffold, and wherein the scaffold is substantially free of heavy metal contaminants;
(b) human cells seeded on the scaffold, and
(c) cell culture medium.

8. The composition of claim 7 wherein the cell culture medium comprises human serum.

9. The composition of claim 7 wherein the human cells comprise smooth muscle cells.

10. The composition of claim 7 wherein the human cells seeded on the scaffold are passaged less than 10 times when seeded.

11. The composition of claim 7, wherein the length of the scaffold is 1 cm to 100 cm.

12. The composition of claim 7, wherein the length of the scaffold is 10 cm to 40 cm.

13. The composition of claim 7, wherein the inner diameter of the scaffold is 3 mm to 6 mm.

14. The composition of claim 7, wherein the scaffold comprises non-biodegradable supports at each end.

* * * * *

UNITED STATES PATENT AND TRADEMARK OFFICE
CERTIFICATE OF CORRECTION

PATENT NO. : 10,619,132 B2  Page 1 of 1
APPLICATION NO. : 15/595560
DATED : April 14, 2020
INVENTOR(S) : Shannon L.M. Dahl et al.

It is certified that error appears in the above-identified patent and that said Letters Patent is hereby corrected as shown below:

On the Title Page

Under (72) Inventors:
Add:
--Juliana Blum, Wake Forest, NC (US)
Heather L. Prichard, Wake Forest, NC (US)--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*